United States Patent [19]

Wright et al.

[11] 4,062,947

[45] Dec. 13, 1977

[54] DI-N-ALKYLAMINOGLYCOSIDES, METHODS FOR THEIR MANUFACTURE AND NOVEL INTERMEDIATES USEFUL THEREIN, METHOD FOR THEIR USE AS ANTIBACTERIAL AGENTS AND PHARMACEUTICAL COMPOSITIONS USEFUL THEREFOR

[75] Inventors: John J. Wright; Peter J. L. Daniels, both of Cedar Grove; Alan K. Mallams, West Orange; Tattanahalli L. Nagabhushan, Parsippany, all of N.J.

[73] Assignee: Schering Corporation, Kenilworth, N.J.

[21] Appl. No.: 706,704

[22] Filed: July 19, 1976

Related U.S. Application Data

[63] Continuation-in-part of Ser. No. 628,637, Nov. 4, 1975, abandoned.

[51] Int. Cl.² .................... A61K 31/71; C07H 15/22

[52] U.S. Cl. ........................... 424/180; 536/4; 536/10; 536/17; 536/18

[58] Field of Search ................ 536/17, 4; 424/180

[56] References Cited

U.S. PATENT DOCUMENTS

| | | | |
|---|---|---|---|
| 3,920,628 | 11/1975 | Daniels | 536/17 |
| 4,002,742 | 1/1977 | Wright et al. | 536/17 |

*Primary Examiner*—Johnnie R. Brown
*Attorney, Agent, or Firm*—Mary S. King; Elizabeth A. Bellamy

[57] ABSTRACT

1,2'-di-N-4,6-di-O-(aminoglycosyl)-1,3-diaminocyclitols and 1,6'-di-N-alkyl-4,6-di-O-(aminoglycosyl)-1,3-diaminocyclitols and their acid addition salts are valuable as antibacterial agents. Also disclosed are 2'-N-alkyl-4,6-di-O-(aminoglycosyl)-1,3-diaminocyclitol antibacterial agents which are also useful as intermediates in the preparation of the 1,2'-di-N-alkyl-4,6-di-O-(aminoglycosyl)-1,3-diaminocyclitols. Preferred compounds of this invention include 1,2'-di-N-ethylsisomicin and 1,6'-di-N-ethylsisomicin.

23 Claims, No Drawings

DI-N-ALKYLAMINOGLYCOSIDES, METHODS FOR THEIR MANUFACTURE AND NOVEL INTERMEDIATES USEFUL THEREIN, METHOD FOR THEIR USE AS ANTIBACTERIAL AGENTS AND PHARMACEUTICAL COMPOSITIONS USEFUL THEREFOR

CROSS REFERENCE TO RELATED APPLICATIONS

This application is a continuation-in-part of co-pending application Ser. No. 628,637 filed Nov. 4, 1975, now abandoned.

FIELD OF THE INVENTION

This invention relates to novel compositions of matter, to methods for their manufacture and methods for their use as antibacterial agents.

More specifically, this invention relates to novel 1,2'-di-N-alkyl-4,6-di-O-(aminoglycosyl)-1,3-diaminocyclitols, 1,6'-di-N-alkyl-4,6-di-O-(aminoglycosyl)-1,3-diaminocyclitols and 2'-N-alkyl-4,6-di-O-(aminoglycosyl)-1,3-diaminocyclitols and antibacterial agents; to pharmaceutical compositions comprising said di-N-alkyl derivatives, to methods for their manufacture and to methods for their use in treating bacterial infections.

Most particularly, this invention relates to 1,2'-di-N-alkyl-, 1,6'-di-N-alkyl-, and 2'-N-alkyl derivatives of 4-O-aminoglycosyl-6-O-garosaminyl-2-deoxystreptamine antibiotics including certain gentamicins, sisomicin, verdamicin, Antibiotics JI-20A and JI-20B, and to 1,2'-di-N-alkyl-, 1,6'-di-N-alkyl-, and 2'-N-alkyl derivatives of related 4-O-aminoglycosyl-6-O-garosaminyl-1,3-di-aminocyclitol antibacterial agents, such as the 5-epi-, 5-epi-azido-5-deoxy-, and 5-epi-amino-5-deoxy analogs of the foregoing and derivatives of Antibiotics Mu-1, Mu-2, Mu-4 and Mu-5.

PRIOR ART

Known in the art (Belgian Patent No. 818,431) are 1-N-alkyl-4,6-di-O-(aminoglycosyl)-2-deoxystreptamines and derivatives thereof which are valuable broad spectrum antibacterial agents possessing improved antibacterial activity over that possessed by the parent antibiotics. Included among these are 1-N-alkyl derivatives of aminoglycosides which have a 6'-N-methyl group in their naturally occurring structure, i.e., 1-N-alkyl derivatives of gentamicins $C_1$ and $C_{2b}$ and of Antibiotic G-52 which may also be named 1-N-alkyl-6'-N-methyl-gentamicins $C_2$ and $C_{1a}$ and 1-N-alkyl-6'-N-methyl-sisomicin, respectively. Unknown in the art, however, are 1,6'-di-N-alkyl derivatives of gentamicins $C_2$ and $C_{1a}$ and of sisomicin having a 6'-N-alkyl group other than -6'-N-methyl. By our invention, heretofore unavailable 1,6'-di-N-alkyl derivatives of gentamicins $C_2$ and $C_{1a}$ and of sisomicin have been discovered which possess an improved spectrum of antibacterial activity over that possessed by the corresponding 1-N-alkyl-6'-N-methylaminoglycoside. For example, 1,6'-di-N-ethyl-sisomicin is active against 6'-N-acetylating microorganisms which are resistant to 1-N-ethyl-6'-N-methyl-sisomicin (known in the art as 1-N-ethyl-Antibiotic G-52).

Also disclosed in the art (e.g. Belgian Patent No. 805,648) are some 2'-N-alkyl-, and some 6'-N-alkyl-4,6-di-O-(aminoglycosyl)-1,3-diaminocyclitol derivatives having antibacterial activity.

By our invention, we have discovered that 1,2'-di-N-alkyl- and 1,6'-di-N-alkyl derivatives of 4,6-di-O-(aminoglycosyl)-1,3-aminocyclitols are valuable antibacterial agents exhibiting greatly enhanced antibacterial activity over that exhibited by the parent antibiotics, and also possessing an improved spectrum of activity compared with that possessed by the corresponding 1-N-alkylaminoglycoside antibacterial agent. For instance, the 1,2'-di-N-alkyl derivatives of this invention are active against 2'-N-acetylating microorganisms, which are resistant to the corresponding 1-N-alkylaminoglycoside precursors.

The advantageously enhanced spectrum of the 1,2'-di-N-alkyl derivatives and of the 1,6'-di-N-alkyl derivatives is surprising in view of our discovery that other di-N-alkyl-4,6-di-O-(aminoglycosyl)-1,3-diaminocyclitols are less active than their parent antibiotics. Thus, for example, 1,3"-di-N-ethylsisomicin and 2',6'-di-N-ethylsisomicin are much less active as antibacterial agents than is sisomicin, and 1,3-di-N-ethyl Antibiotic JI-20B is less active than Antibiotic JI-20B. Moreover, we have also discovered that certain 1,2',6'-tri-N-alkylaminoglyccsides possess reduced antibacterial activity compared with that of their 1,2',6'-tri-N-unsubstituted precursors, even though the corresponding 1,2'-and 1,6'-di-N-alkyl derivatives are potent antibacterial agents. By our invention, therefore, we have discovered that, of the possible di-N-alkyl derivatives which possess one alkyl group at the 1-amino position, only the 1,2'-di-N-alkyl and 1,6'-di-N-alkyl derivatives of our invention possess enhanced antibacterial activity.

GENERAL DESCRIPTION OF THE INVENTION

Composition-of-Matter Aspect

The composition-of-matter aspects of this invention include 1,2'-di-N-X and 1,6'-di-N-X derivatives of 4,6-di-O-(aminoglycosyl)-1,3-diaminocyclitol antibacterial agents wherein the 4-O-aminoglycosyl unit has amino groups all of which are primary, said primary amino groups being on one or both of positions 2'and 6'and wherein X is a substituent selected from the group consisting of alkyl, alkenyl, cycloalkylalkyl, aralkyl, hydroxyalkyl, aminoalkyl, alkylaminoalkyl, aminohydroxyalkyl and alkylaminohydroxyalkyl, said substituent having 2 to 8 carbon atoms, the carbon in said substituent adjacent to the aminoglycoside nitrogen being unsubstituted, and when said substituent is substituted by both amino and hydroxyl functions, only one of said functions can be attached at any one carbon atom; and wherein the substituent, X, in said 1,2'-di-N-X and 1,6'-di-N-X derivatives may be the same or different and the pharmaceutically acceptable acid addition salts thereof.

Included among the alkyl substituents contemplated for the moiety "X" in our novel compounds are straight and branched chain alkyl groups such as ethyl, n-propyl, n-butyl, β-methylpropyl, n-pentyl, β-methylbutyl, γ-methylbutyl and β,β-dimethylpropyl: n-hexyl, δ-methylpentyl, β-ethylbutyl, γ-ethylbutyl, n-heptyl, ε-methylheptyl, β-ethylpentyl, γ-ethylpentyl, γ-ethylpentyl, γ-propylbutyl, n-octyl, iso-octyl,β-ethylhexyl, γ-ethylhexyl, ε-ethylhexyl, β-propylpentyl, γ-propylpentyl; cycloalkylalkyl, groups such as cyclopropylmethyl, cyclopentylmethyl, cyclohexylmethyl and cyclopentylethyl; alkenyl groups such as β-propenyl, β-methylpropenyl, β-butenyl, β-methyl-β-butenyl, β-ethyl -β-hexenyl: aralkyl groups such as benzyl, o-xylyl, m-xylyl, p-xylyl and phenylethyl: hydroxy substituted straight and branched chain alkyl groups such as ε-hydroxypentyl, β-hydroxy-γ-methylbutyl, β-hydroxy-β-methylpropyl, δ-hydroxybutyl, β-hydroxypropyl, γ-hydroxypropyl ω-hydroxyoctyl; amino substituted straight and branched chain alkyl groups such as [65-aminopentyl, β-aminopropyl, γ-aminopropyl, δ-aminobutyl, β-amino-γ-methylbutyl and ω-aminooctyl and mono-N-alkylated derivatives thereof such as the N-methyl, N-ethyl, and N-propyl derivatives, e.g. ε-methylaminopentyl. β-methylaminopropyl, β-ethylaminopropyl, δ-methylaminobutyl, β-methylamino-γ-methylbutyl, and ω-methylaminobutyl; amino and hydroxy disubstituted straight and branched chain alkyl groups such as β-hydroxy-ε-aminopentyl, γ-hydroxy- γ-methyl- δ-aminobutyl, β-hydroxy-δ-aminobutyl, β-hydroxy-γ-aminopropyl, and β-hydroxy-β-methyl-γ-aminopropyl; and mono-N-alkylated derivatives thereof such as β-hydroxy-ε-methyl-aminopentyl, γ-hydroxy-γmethyl- δ-methylaminobutyl, β-hydroxy- δ-methylaminobutyl, β-hydroxy-δ-ethylaminopropyl, and β-hydroxy-β-methyl-γ-methylaminopropyl.

Of the foregoing substituents "X", preferred are lower alkyl substituents having 2 to 4 carbon atoms. Particularly, valuable alkyl derivatives are the ethyl, propyl, n-butyl, iso-butyl, γ-aminopropyl, δ-aminobutyl, β-hydroxyethyl, δ-amino-β-hydroxybutyl, and γ-amino-β-hydroxypropyl derivatives of this invention.

The 1,2'-di-N-X and 1,6'-di-N-X derivatives of 4,6-O-(aminoglycosyl)-1,3-diaminocyclitols wherein said 6-O-aminoglycosyl is 6-O-garosaminyl, are particularly useful and include the 1,2'-di-N-X-4-O-(aminoglycosyl)-6-O-garosaminyl-1,3-diaminocyclitols selected from the group consisting of:

1,2'-di-N-X-gentamicin $C_1$ a,
1,2'-di-N-X-gentamicin $C_2$,
1,2'-di-N-X-gentamicin $C_2$a,
1,2'-di-N-X-gentamicin $X_2$,
1,2'-di-N-X-sisomicin,
1,2'-di-N-X-verdamicin,
1,2'-di-N-X-Antibiotic G-418,
1,2'-di-N-X-Antibiotic JI-20A,
1,2'-di-N-X-Antibiotic JI-20B, the 5-epi-, 5-epi-azido-5-deoxy-, 5-epi-amino-5-deoxy analogs of the foregoing and,
1,2'-di-N-X-Antibiotic Mu-1,
1,2'-di-N-X-Antibiotic Mu-2,
1,2'-di-N-X-Antibiotic Mu-4 and
1,2'-di-N-X-Antibiotic Mu-5;

wherein X is as hereinabove defined; and the pharamaceutically acceptable acid addition salts thereof.

The foregoing 1,2'-di-N-X-derivatives are valuable antibacterial agents, exhibiting enhanced antibacterial activity over the corresponding 1,2'-di-N-unsubstituted precursors and an improved spectrum of activity over that of the corresponding 1-N-alkyl dervatives. For example, 1,2'-di-N-ethylsisomicin is active against 2'-N-acetylating microorganisms which are resistant to 1-N-ethylsisomicin.

Another composition-of-matter aspect of this invention includes the 1,6'-di-N-X-4-O-(aminoglycosyl)-6-O-garosaminyl-1,3-diaminocyclitols selected from the group consisting of:

1,6'-di-N-X-gentamicin B,
1,6'-di-N-X-gentamicin $B_1$,
1,6'-di-N-X-gentamicin $C_1$a,
1,6'-di-N-X-gentamicin $C_2$,
1,6'-di-N-X-gentamicin $C_2$a,
1,6'-di-N-X-sisomicin,
1,6'-di-N:X-verdamicin,
1,6'-di-N:X-Antibiotic JI-20A,
1,6'-di-N-X-Antibiotic JI-20B, The 5-epi, 5-epi-azido-5-deoxy, 5-epi-amino-5-deoxy analogs of the foregoing and,
1,6'-di-N-X-Antibiotic Mu-1,
1,6'-di-N-X-Antibiotic Mu-2,
1,6'-di-N-X-Antibiotic Mu-4,
1,6'-di-N-X-Antibiotic Mu-5;

wherein X is as hereinabove defined; and the pharmaceutically acceptable acid addition salts thereof.

The foregoing 1,6'-di-N-X derivatives exhibit enhanced antibacterial activity over that of the corresponding 1,6'-di-N-unsubstituted precursors and an improved spectrum of activity over that exhibited by the corresponding 1-N-alkyl dervatives. For example, 1,6'-di-N-ethylsisomicin is active against 6'-N-acetylating microoganisms resistant to 1-N-ethylsisomicin.

Our invention preferentially embraces those 1,2'-di-N-X and 1,6'-di-N-X-4,6-di-O-(aminoglycosyl)-1,3-diaminocyclitols wherein said 6-O-aminoglycosyl is 6-O-garosaminyl and said 1,3-diaminocyclitol is 2-deoxystreptamine; including the 1,2'-di-N-X derivatives of gentamicin $C_1$a, $C_2$, $C_2$a, $X_2$, sisomicin, verdamicin, Antibiotic G-418, JI-20A, JI-20B, and the 1,6'-di-N:X-derivatives of gentamicin B, $B_1$, $C_1$a, $C_2$, $C_2$a, sisomicin, verdamicin, Antibiotic JI-20A, and JI-20B.

Additionally preferred compounds of our invention are the 1,2'-di-N:X- and 1,6'-di-N-X-derivatives of Antibiotic 66-40D, which derviatives possess enhanced antibacterial activity over the parent antibiotic.

As disclosed hereinabove, the substitutent, X, may be the same or different in the foregoing 1,2'-di-N-X- and 1,6'-di-N-X-4,6-di-O-(aminoglycosyl)-1,3-diaminocyclitols of this invention. Thus the preferred compounds of our invention include sisomicin derivatives such as 1,2'-di-N-ethylsisomicin, 1,6'-di-N-ethylsisomicin, 1,2'-di-N-propylsisomicin, 1,6'-di-N-propylsisomicin, 1,2'-di-N-(γ-aminopropyl)sisomicin, 1,6'-di-N-(γ-aminopropyl)sisomicin, 1,2'-di-N-(γ-aminobutyl)sisomicin, 1,6'-di-N-(γ-aminobutyl)sisomicin, and mixed di-N-alkyl dervatives such as 1-N-ethyl-2'-N-propylsisomicin, 1-N-ethyl-6'-N-propylsisomicin, 1-N-ethyl-2'-N-(γ-aminobutyl)sisomicin and 1-N-ethyl6'-N-(γ-aminobutyl)sisomicin.

Still another composition-of-matter aspect of this invention relates to 2'-N-X-4,6-di-O-(aminoglycosyl)-1,2-diaminocyclitols selected from the group consisting of:

2'-N-X-gentamicin A,
2'-N-X-sisomicin,
2'-N-X-verdamicin,
2'-N-X-tobramycin,
2'-N-X-Antibiotic 66-40B,
2'-N-X-Antibiotic 66-40D, The 5-epi, 5-epi-azido-5-deoxy, 5-epi-amino-5-deoxy analogs of the foregoing; and
2'-N-X-Antibiotic Mu-1, 2'-N-X-Antibiotic Mu-2,
2'-N-X-Antibiotic Mu-4 -and
2'-N-X-Antibiotic Mu-5;

and the 5-epi-, 5-epi-azido-5-deoxy,5-epi-amino-5-deoxy analogs of the following:

2'-N-X-gentamicin $C_1a$,
2'-N-X-gentamicin $C_2$,
2'-N-X-gentamicin $C_2a$,
2'-N-X-gentamicin $X_2$,
2'-N-X-Antibiotic G-418,
2'-N-X-Antibiotic JI-20A,
2'-N-X-Antibiotic JI-20B;

wherein X is as hereinabove defined and the pharmaceutically acceptable acid addition salts thereof.

The foregoing 2'-N-X-4,6-di-O-(aminoglycosyl)-1,3-diaminocyclitols exhibit antibacterial activity per se; however, their primary usefulness is as intermediates in the preparation of the corresponding 1,2'-di-N-X-aminoglycosides as described in detail hereinbelow.

Also included within the composition-of-matter aspect of this invention are pharmaceutically acceptable acid addition salts of the 1,2'-di-N-X-, and the 1,6'-di-N-X- and 2'-N-X-4,6-di-O-(aminoglycosyl)-1,3-diaminocyclitols described hereinabove, which are made according to known procedures such as by neutralizing the free base with the appropriate acid usually to about pH 5.

Included among the pharmaceutically acceptable acid addition salts of this invention are those derived from organic acids such as acetic acid, propionic acid, succinic acid, fumaric and maleic acid, or preferably, from inorganic acids such as hydrochloric, sulfuric, phosphoric acid hydrobromic. the physical embodiments of the acid addition salts of this invention are characterized by being white solids which are soluble in water, sparingly soluble in most polar organic solvents and insoluble in most non-polar organic solvents.

PROCESS ASPECT OF INVENTION

One process aspect of this invention is the preparation of a 1,2'-di-N-X- or a 1,6'-di-N-X-derivative of a 4,6-di-O-(aminoglycosyl)-1,3-diaminocylitol wherein each X may be the same or different and is a substituent selected from the group consisting of alkyl, alkenyl, cycloalkylalkyl, aralkyl, hydroxyalkyl, aminoalkyl, alkylaminoalkyl, aminohydroxyalkyl and alkylaminohydroxyalkyl, said substituent having 2to 8 carbon atoms, the carbon in said substituent adjacent to the aminoglycoside nitrogen being unsubstituted and when said substituent is substituted by both hydroxyl and amino functions, only one of said functions can be attached at any one carbon atom.

This process comprises treating an acid addition salt of a member selected from the group consisting of a 4,6-di-O-(aminoglycosyl)-1,3-diaminocyclitol antibacterial agent; said 4-O-aminoglycosyl having amino groups all of which are primary, said primary amino groups being on one or both of positions 2' and 6'; and the 1-N-X, 2'-N-X-and 6'-N-X- derivatives thereof; with from about 0.5 to about 2 molar equivalents of a hydride-donor reducing agent in an inert solvent and with at least one equivalent of an aldehyde having the formula X'CHO wherein X' is a substituent selected from the group consisting of alkyl, alkenyl, alkylcycloalkyl, aralkyl, hydroxyalkyl, aminoalkyl, alkyaminoalkyl, aminohydroxyalkyl and alkylaminohydroxyalkyl, said substituents having up to 7 carbon atoms, and, when said substituent is substituted by both hydroxyl and amino functions, only one of said functions can be attached to any one carbon atom; and isolating the 1,2' or 1,6'-di-N-X-4,6-di-o-(aminoalglycosyl)-1,3-diaminocyclitol thereby formed.

this process whereby the 1,2' and 1,6' amino functions in an acid addition salt of a 4,6-di-O-(aminoglycosyl)-1,3-diamino cyclitol antibacterial agent, said 4-O-aminoglycosyl having amino groups all of which are primary, said primary amino groups being on one or both of positions 2' and 6', are selectively condensed with and aldehyde and concomitantly reduced in situ to form a 1,2'-di-N-X- or a 1,6'-di-N-X-4,6-di-O-(aminoglycosyl)-1,3-diaminocyclitol antibacterial agent, is usually carried out at 0° C to room temperature in the presence of air, although it may be advantageously carried out under an inert atmosphere (e.g. argon or nitrogen). The reaction is completed within 1-2 hours as determined by thin layer chromatography.

Hydride-donor reducing agents useful in our process include dialkylaminoboranes (e.g. dimethylaminoborane, diethylaminoborane and preferably morpholinoborane), tetraalkylammonium cyanoborohydride (e.g. tetrabutylammonium cyanoborohydride), akali-metal borohydride (e.g. sodium borohydride) and preferably alkali-metal cyanoborohydride (e.g. lithium cyanoborohydride and sodium cyanoborohydride).

Our process is conveniently carried out at ambient temperatures in an inert solvent. By "inert solvent" is meant any organic or inorganic solvent in which the 4,6-di-(aminoglycosyl)-1,3-diaminocyclitol starting compounds and/or their 1-N-X-, 2'-N-X,6'-X derviatives and the reagents are soluble, and which will not interfere with the process under the reaction conditions thereof, so there are produced minimum of competing side reactions. Although anhydrous aprotic solvents may sometimes advantageously be employed in our process (such as tetrahydrofuran when utilizing morpholinoborane as hydride-donor reducing agent) we usually carry out our process in protic solvents, e.g. in a lower alkanol or, preferably, in water or in an aqueous lower alkanol (e.g. aqueous methanol, aqueous ethanol), although other water-miscible co-solvent systems may be employed such as aqueous dimethylformamide, aqueous hexamethylphosphoramide, aqueous tetrahydrofuran and aqueous ethylene glycol dimethyl ether.

the acid addition salts of 4,6-di(aminoglycosyl)-1,3-diaminocyclitols or their 1-N-X, 2'-N-X dervatives, requisite starting compounds of our process, may be derived from any organic acid such as acetic acid, trifluoracetic acid, or p-toluenesulfonic acid or from any inorganic acid such as hydrochloric acid, sulfuric acid or phosphoric acid. We have found it most convenient to use the addition salts derived from sulfuric acid. In carrying out our process, we find it convenient to prepare the requisite acid addition salt starting compound in situ by adding the desired acid (e.g. sulfuric acid) to a solution or suspension of the 4,6-di-O-(aminoglycosyl)-1,3-diaminocyclitol(e.g. sisomicin) in a protic solvent (e.g. water) until the pH of the solution is in the range of from about 2 to about 5, preferably from about pH 2.5 to about pH 3.5. Our process proceeds best within this range, but may be carried out at pH values in the range of from about pH 1 to about pH 8.

The starting acid addition salts of this process can be derived from a 4,6:di-O-(aminoglycosyl)-1,3- diaminocyclitol having a primary amine on one or both of positions C-2'- or C-6', and/or its 1-N-X, 2'-N-X, 6'-N-X derivatives which exibit antibacterial activity against gram-positive and/or gram-negative organisms as determine by conventional in vitro techniques. Inhibition of bacteria at concentrations equal to or less than about 50 to 100 mcg/ml is the sine qua non of an antibactieral agent.

Typical 4,6-di-O-(aminoglycosyl)-1,3-diaminocyclitol antibacterial precursors for the acid addition salt starting compounds of our invention include 4-O-aminoglycosyl-6-O-garosaminyl-2-deoxystreptamine antibiotics such as gentamicin B, gentamicin B$_1$, gentamicin C$_1$a, gentamicin C$_2$, gentamicin C$_2$a, gentamicin X$_2$, sisomicin, verdamicin, Antibiotic G-418, Antibiotic JI-20A, and Antibiotic JI-20B, the 5-epi, 5-epi-azido-5-deoxy-, and 5-epi-amino-5-deoxyanalogs of the foregoing;

4,6-di-O-(aminoglycosyl)-2-deoxystreptamines such as gentamicin A, tobramycin, Antibiotic 66-40B and Antibiotic 66-40D;

their 5-epi, 5-epi-azido-5-deoxy, 5-epi-amino-5-deoxy analogs; and related 4,6-di-O-(aminoglycosyl)-1,3-diaminocyclitols such as Antibiotics Mu-1, Mu-2, Mu-4 and Mu-5.

Of the foregoing, preferred starting antibiotic precursors are gentamicins B, C$_1$a, C$_2$, C$_2$a, Antibiotic 66-40D verdamicin, and particularly, sisomicin, all of which lead to preferred compounds of this invention i.e., to the corresponding 1,2'-di-N-alkyl and/or the 1,6'-di-N-alkyl derivatives.

The following formulae I - V illustrate the starting compounds of an invention.

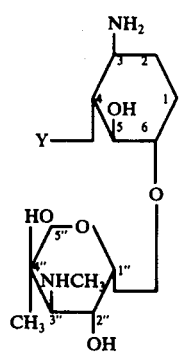

I

Wherein Y is an aminoglycosyl function selected from the group consisting of:

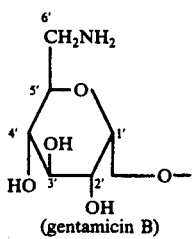
(gentamicin B)

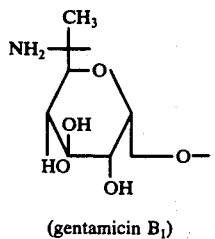
(gentamicin B$_1$)

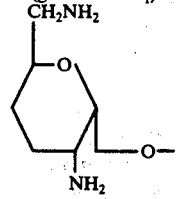

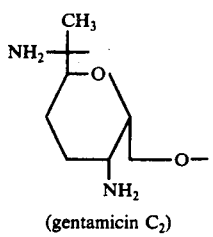
(gentamicin C$_2$)

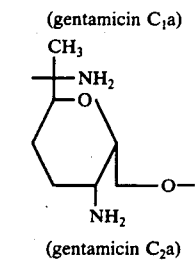
(gentamicin C$_1$a)

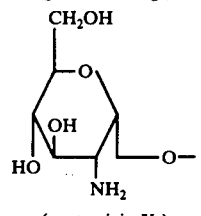
(gentamicin C$_2$a)

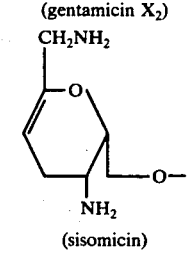
(gentamicin X$_2$)

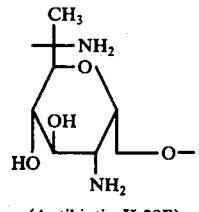
(verdamicin)

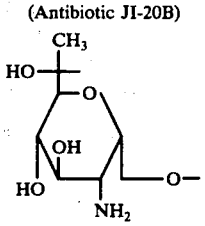
(sisomicin)

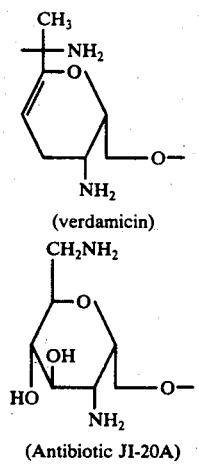
(Antibiotic JI-20A) (Antibiotic JI-20B)

(Antibiotic G-418)

Tobramycin of the following formula II:

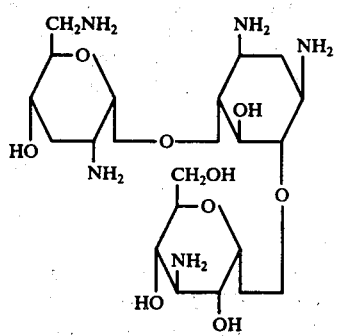

Antibiotic 66-40D of the following formula III:

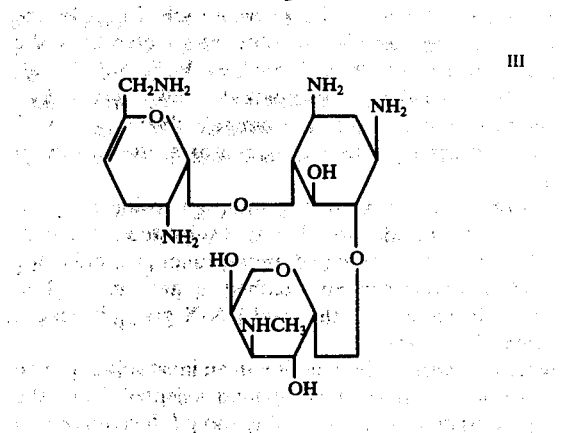

Gentamicin A and Antibiotic 66-40B of the following formula IV:

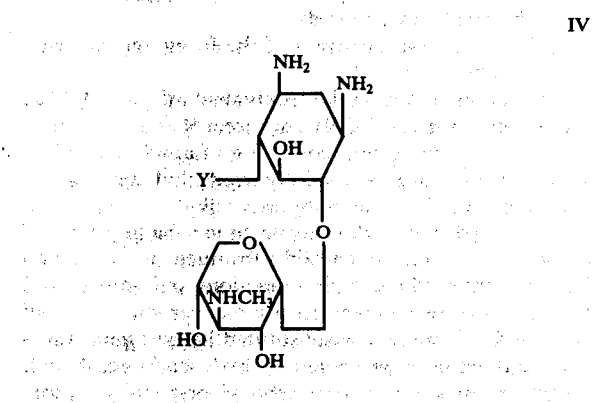

wherein Y' is (Gentamicin A)

and Y' is

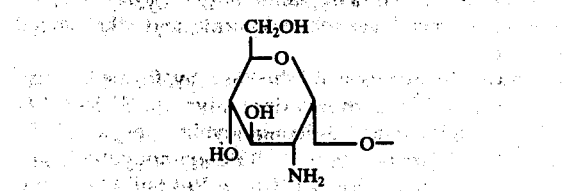

(Antibiotic 66-40B)

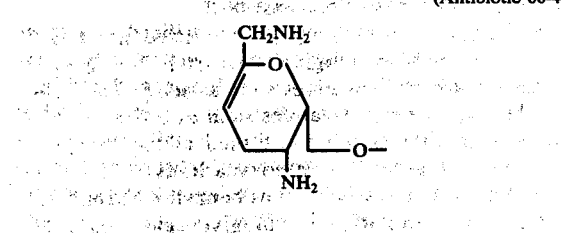

Antibiotics Mu-1, Mu-2, Mu-4 and Mu-5 are defined by the following formula V:

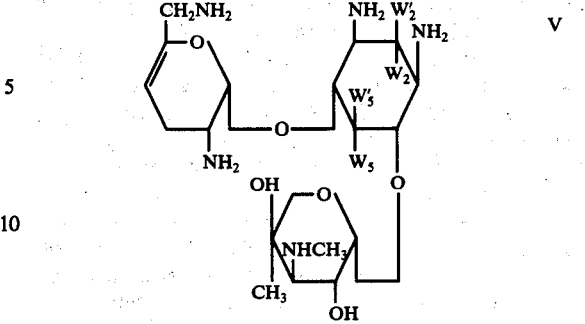

in Antibiotic Mu-1, $W_2'$, $W_5$ are hydrogen and $W_2$ and $W_5'$ are hydroxy;

in Antibiotic Mu-2, $W_2$, $W_2'$, $W_5$ and $W_5'$ are hydrogen;

in Antibiotic Mu-4, $W_2'$ and $W_5'$ are hydroxy and $W_2$ and $W_5$ are hydrogen; and in Antibiotic Mu-5, $W_2$, $W_2'$, and $W_5$ are hydrogen while $W_5'$ is amino.

All of the aforementioned 4,6-di-O-(aminoglycosyl)-1,3-diaminocyclitol antibiotics are known. Antibiotics Mu-1, Mu-2, Mu-4 and Mu-5 are synomously known as the corresponding mutamicins 1, 2, 4 and 5, described in Belgian Patent No. 818,429 published Feb. 3, 1975 which corresponds to co-pending application U.S. Ser. No. 476,638 filed June 5, 1974, now U.S. Pat. No 4,011,390 issued May 8, 1977.

Additionally the 1-N-alkyl-4,6-di-O-(aminoglycosyl)-1,3-diaminocyclitol antibacterial precursors are described in Belgian Patent No. 818,431 and in our co-pending U.S. application Ser. No. 492,998 filed July 30, 1974, now U.S. Pat. No. 4,002,742, issued Jan. 11, 1977. The 1-N-alkyl-5-epiamino-5-deoxy and 1-N-alkyl-5-epiazido-5-deoxy-4,6-di-O-(aminoglycosyl)-1,3-diaminocyclitol precursors are described in co-pending U.S. Application Ser. No. 611,290 filed Sept. 8, 1975 of Peter Daniels, now U.S. Pat. No. 4,000,262, issued Dec. 28, 1976. The 1-N-alkyl-5-epi-4,6-di-O-(aminoglycosyl)-1,3-diaminocyclitol precursors are described in co-pending U.S. application Ser. No. 611,289 filed Sept. 8, 1975 of Peter Daniels, now U.S. pat. No. 4,000,261 issued Dec. 28, 1976. The 6'-N-alkyl-4,6-di-O-(aminoglycosyl)-1,3-diaminocyclitol precursors are prepared as described in co-pending U.S. application Ser. No. 574,070 filed May 2, 1975 of Peter Daniels, now abandoned, and in co-pending U.S. application Ser. No. 596,799 filed July 17, 1975 of Alan Mallams, which is equivalent to Belgian Patent No. 805,648.

Typical aldehydes of the formula X'CHO wherein X' is as above defined which are useful in our process include straight and branched chain alkyl aldehydes such as acetaldehyde, n-propanal, n-butanal, 2-methylpropanal, n-pentanal, 2-methylbutanal, 3-methylbutanal, 2,2-dimethylpropanal, n-hexenal, 2-ethylbutanal, n-heptanal and n-octanal: cycloalkylaldehydes such as cyclopropanecarboxaldehyde, cyclopentanecarboxaldehyde, cyclopentaneacetaldehyde, and cyclohexanecarboxaldehyde: alkenyl aldehydes such as propenal, 2-methylpropenal, 2-butenal, 2-methyl-2-butenal, 2-ethyl-2-hexenal; aralkyl aldehydes such as benzaldehyde, o,m, and p-tolualdehydes and phenylacetaldehyde: hydroxy substituted straight and branched chain alkyl aldehydes such as 5-hydroxypentanal, 2-hydroxy-3-methylbutanal, 2-hydroxy-2-methylpropanal, 4- hydroxybutanal, 2-hydroxypropanal and 8-hydroxyoctanal: amino substituted straight and branched chain alkyl aldehydes such as 5-aminopentanal, 2-aminopropanal, 3-aminopropanal, 4-aminobutanal, 2-amino-3-methylbutanal, 8-aminooctanal and mono-N-alkyl derivatives thereof; and amino and hydroxy disubstituted straight and branched chain alkyl aldehydes such as 2-hydroxy-5-aminopentanal, 3-hydroxy-3-methyl-4-aminobutanal, 2-hydroxy-4-aminobutanal, 2-hydroxy-3-aminopropanal, 2-hydroxy-2-methyl-3-aminopropanal, 2-amino-3-hydroxyoctanal, and mono-N-alkyl derivatives thereof.

In this process, if the aldehyde possesses a chiral center, one can use each enantiomer separately or together as a racemate and there will be obtained the respective diastereoisomers or a mixture thereof, respectively.

The aldehyde reagents useful in our process are either known compounds or are easily prepared from known compounds utilizing procedures well known in the art.

When carrying out our process utilizing an amino aldehyde as the reagent, in order to minimize competing side reactions, it is essential to protect the amino function in the aldehyde e.g. with an acyl blocking group such as acetamido, phthalmido or the like prior to carrying out our process, and thence de-protecting at a convenient later time. It may also be advantageous to protect the hydroxyl group in hydroxyl containing aldehydes when carrying out our process, however, it is not generally necessary.

A convenient method of carrying out our process comprises preparing a solution of a 4,6-di-O-(aminoglycosyl)-1,3-diaminocyclitol or 1-N-X, 2'-N-X, 6'-N-X antibacterial agent (e.g. sisomicin) in a protic solvent, (preferably water), and adjusting the pH of the solution to from about pH 2 to about pH 5 with an acid (usually dilute sulfuric acid) thereby preparing the requisite acid addition salt of the starting compound. When the pH of the solution is at about pH 5, the acid addition salt thereby produced usually contains about one equivalent of acid for each amino function in the 4,6-di-O-(aminoglycosyl)-1,3-diaminocyclitol (e.g. per mole of sisomicin there is present 2.5 moles of sulfuric acid). After the acid addition salt solution is prepared, there is added at least a molar equivalent, and preferably a large molar excess of the desired aldehyde (e.g. acetaldehyde) followed within a short time (usually in about 5 minutes) by the addition of from about 0.5 to about 2 molar equivalents (based upon the starting 4,6-di-O-(aminoglycosyl)-1,3-diaminocyclitol) of a hydride-donor reducing reagent, preferably an alkali metal cyanoborohydride, usually sodium cyanoborohydride. The reaction is frequently completed in 1-2 hours as determined by thin layer chromatography and there is obtained the corresponding 1,2'-di-N- and/or 1,6'-di-N-alkyl-4,6-di-O-(aminoglycosyl)-1,3-diaminocyclitol (e.g. 1,2'-di-N-ethylsisomicin) having enhanced antibacterial activity.

In the foregoing process, the quantity of hydride-donor reducing agent most advantageously used to produce maximum yields of di-N-alkyl derivatives is from about 1 to 2 molar equivalents per mole of N-unprotected-4,6-di-O-(aminoglycosyl)-1,3-diaminocyclitol, and from about 0.5 to about 1 molar equivalent per mole of a 1-N-alkyl-, or a 2'-N-alkyl-, or a 6'-N-alkyl-4,6-di-O-(aminoglycosyl)-1,3-diaminocyclitol.

Still another process aspect of our invention is the preparation of a 2'-N-X or a 1,2'-di-N-X-derivative of a 4,6-di-O-(aminoglycosyl)-1,3-diaminocyclitol antibacterial agent, said 4-O-aminoglycosyl having a primary amino group at position 2', wherein each X may be the same or different and is a substituent selected from the group consisting of alkyl, alkenyl, cycloalkylalkyl, aralkyl, hydroxyalkyl, aminoalkyl, alkylaminoalkyl, aminohydroxyalkyl and alkylaminohydroxyalkyl, said substituent having 2 to 8 carbon atoms, the carbon in said substituent adjacent to the aminoglycoside nitrogen being unsubstituted, and when said substituent is substituted by both hydroxyl and amino functions, only one of said functions can be attached at any one carbon atom; with the proviso that said 1-N-X group is devoid of amino functions;

which comprises the reaction in an inert solvent of an acid addition salt of a compound selected from the group consisting of a 1,3-N,N'-carbonyl derivative of a 4,6-di-O-(aminoglycosyl)-1,3-diaminocyclitol; a 1,3-N,N'-carbonyl-6'-N-Y-derivative of a 4,6-di-O-(aminoglycosyl)-1,3-diaminocyclitol having a primary carbinamine at C-5'; Y being a hydrocarboncarbonyl having up to 8 carbon atoms, benzyloxycarbonyl, alkoxycarbonyl, or trichloroethoxycarbonyl;

and the 1-N-X-derivatives of the foregoing, X being as hereinabove defined;

with at least one molar equivalent of an aldehyde having the formula R-CHO, wherein R is a substituent selected from the group consisting of alkyl, cycloalkylalkyl, alkenyl, aryl, aralkyl, hydroxyalkyl, aminoalkyl, alkylaminoalkyl, aminohydroxyalkyl, and alkylaminohydroxyalkyl, said substituent having up to 7 carbon atoms and, when said substituent is substituted by both hydroxyl and amino functions, only one of said functions can be attached to any one carbon atom; and when said substituent is substituted by an amino function, said amino is protected by hydrocarboncarbonyl, benzyloxycarbonyl, alkoxycarbonyl or trichloroethoxycarbonyl;

and thence reaction with at least from about 0.5 to about 2 molar equivalents of a hydride-donor reducing agent selected from the group consisting of dialkylaminoborane, tetraalkylammonium cyanoborohydride, alkali metal cyanoborohydride and alkali metal borohydride;

followed by reaction of the thereby formed corresponding 1,3-N,N'-carbonyl derivative of a 2'-N-X-4,6-di-O-(aminoglycosyl)-1,3-diaminocyclitol or a 1,2'-di-N-X-4,6-di-O-(aminoglycosyl)-1,3-diaminocyclitol, or of a 2'-N-X- or a 1,2'-di-N-X-6'-N-Y-4,6-di-O-(aminoglycosyl)-1,3-diaminocyclitol having a primary carbinamine at C-5, with hydrazine hydrate in water.

In this process, the R-CHO aldehydes, the quantity of hydride-donor reducing agent, the solvents and reaction conditions used are similar to those described hereinabove for our other process aspect.

The Y-amino protecting groups utilized are those well known in the aminoglycoside art including hydrocarboncarbonyl derivatives such as acetyl and benzoyl; alkoxycarbonyl derivatives such as ethoxycarbonyl and t-butoxycarbonyl; substituted alkoxycarbonyl derivatives such as trichloroethoxycarbonyl and aralkyloxycarbonyl derivatives such as benzyloxycarbonyl.

The 1,3-N,N'-carbonyl aminoglycoside requisite starting compounds of this process are prepared as described in the Preparations hereinbelow by reacting a fully N-protected alkoxycarbonyl or aralkoxycarbonyl derivative (or substituted derivatives thereof) of an aminoglycoside having a primary amine at the C-2' position in the 4-O-aminoglycosyl moiety, with sodium hydroxide at elevated temperatures whereby the benzyloxy groups at the 1 and 3 positions together form a cyclic carbonyl derivative and the other N-benzyloxycarbonyl groups are cleaved whereby is obtained the 1,3-N,N'-carbonyl derivatives of the 4,6-di-O-(aminoglycosyl)-1,3-diaminocyclitol. This may also be accomplished by utilizing the 1-N-ethyl derivatives of the fully N-protected aminoglycoside to obtain a 1-N-ethyl-1,3-N,N'-carbonyl-4,6-di-O-(aminoglycosyl)-1,3-diaminocyclitol.

In the foregoing 1,3-N,N'-carbonyl derivative, it is sometimes desirable to protect any primary carbinamine at position C-5' on the 4-O-aminoglycosyl ring by reacting the 1,3-N,N'-carbonyl or 1-N-alkyl-1,3-N,N'-carbonyl derivatives of the aminoglycosides with acetyl imidazole and isolating the thereby produced 1,3-N,N'-carbonyl-6'-N-acetyl- and 1,3-N,N'-carbonyl-6'-N-acetyl-1-N-alkyl derivatives.

In this process, the 1,3-N,N'-carbonyl, 1,3-N,N'-carbonyl-1-N-alkyl-, 1,3-N,N'-carbonyl-6'-N'-acetyl-, and 1,3-N,N'-carbonyl-6'-N-acetyl-1-N-alkyl derivatives of the 4,6-di-O-(aminoglycosyl)-1,3-diaminocyclitols are reacted with a hydride donor reducing agent such as sodium cyanoborohydride and an aldehyde, RCHO, R being as defined hereinabove, in an acid media to obtain the corresponding 2'-N- or 1,2'-di-N-alkyl derivative of the foregoing 1,3-N,N'-carbonyl-4,6-di-O-(aminoglycosyl)-1,3-diaminocyclitol or 1-N-alkyl and/or 6'-N-acetyl derivative thereof. Reaction of the foregoing with hydrazine hydrate cleaves the N-protecting groups to produce the corresponding 2'-N-alkyl or 1,2'-di-N-alkyl derivatives of the 4,6-di-O-(aminoglycosyl)-1,3-diaminocyclitol.

The invention described hereinabove is illustrated in detail hereinbelow in the Preparations and Examples which should not be construed as limiting the scope of my invention.

PREPARATION OF INTERMEDIATES

PREPARATION I

A. 1,3-N,N'-Carbonylsisomicin and 1,3-N,N'-Carbonyl-1-N-ethylsisomicin

1. Reflux a solution of 10 gm. of 1,3,2',6',3''-penta-N-benzyloxycarbonylsisomicin in 10% aqueous dioxane containing 5% by weight of sodium hydroxide for 24 hours. Remove the organic solvent by evaporation. Pass the resultant aqueous residue down a column of Amberlite IRC-50 (H+) ion exchange resin. Elute the column with 3% ammonium hydroxide, concentrate the eluate and chromatograph the resultant residue on silica gel in the lower phase of a chloroform-methanol-15% aqueous ammonium hydroxide (2:1:1) system. Combine like fractions as determined by thin layer chromatography. Concentrate to remove the organic solvents, and lyophilize the resultant aqueous solution to obtain 1,3-N,N'-carbonylsisomicin.

2. In the foregoing procedure by utilizing 1,3,2',6',3''-penta-N-benzyloxycarbonyl-1-N-ethylsisomicin as the starting compound there is obtained 1,3-N,N'-carbonyl-1-N-ethylsisomicin.

B. 1,3-N,N'-Carbonylaminoglycosides and 1,3-N,N'-Carbonyl-1-N-Ethylaminoglycosides 1. In a manner similar to that described in Preparation IA1, treat with sodium hydroxide in dioxane the per-N-benzyloxycarbonyl derivatives of the following aminoglycosides:

Gentamicin A,
Gentamicin C$_{1a}$,
Gentamicin C$_2$,
Gentamicin C$_{2a}$,
Gentamicin X$_2$,
Verdamicin,
Tobramycin,
Antibiotic G-418,
Antibiotic 66-40B,
Antibiotic 66-40D,
Antibiotic JI-20A,
Antibiotic JI-20B, the 5-epi, 5-epi-azido-5-deoxy and 5-epi-amino-5-deoxy analogs of the foregoing and of sisomicin;
and Antibiotic Mu-1, Antibiotic Mu-2, Antibiotic Mu-4, and Antibiotic Mu-5.

Isolate and purify the resultant products in a manner similar to that described to obtain the corresponding 1,3-N,N'-carbonylaminoglycosides.

2. In the foregoing procedure, by utilizing the per-N-benzyloxycarbonyl-1-N-ethyl derivative of the aforementioned aminoglycosides as starting compound, there is obtained the corresponding 1,3-N,N'-carbonyl-1-N-ethylaminoglycoside.

C. 1,3-N,N'-Carbonyl-1-N-alkylaminoglycosides

In the procedure of Preparation IA1, utilize as starting compounds other per-N-benzyloxycarbonyl-1-N-alkyl derivatives of the aminoglycosides starting compounds of Preparation IB1; such as the per-N-benzyloxycarbonyl-1-N-propyl and the per-N-benzyloxycarbonyl-1-N-butyl derivatives to obtain the corresponding 1,3-N,N'-carbonyl-1-N-alkylaminoglycosides.

PREPARATION II

A. 1,3-N,N'-Carbonyl-6'-N-acetylsisomicin and 1,3-N,N'-Carbonyl-6'-N-acetyl-1-N-ethylsisomicin 1. To a stirred solution of 1,3-N,N'-carbonylsisomicin (4.5 gm) in 50 ml. of methanol, add at 0°–4° C over a period of 10 minutes, a solution of acetylimidazole (1.1 gms.) in 10 ml. of tetrahydrofuran. Stir for 2 hours, remove the solvent by evaporation and chromatograph the resultant residue on silica gel in the lower phase of a mixture of chloroform-methanol-10% aqueous ammonium hydroxide (2:1:1), combine like fractions as determined by thin layer chromatography, remove the organic solvents by evaporation and lyophilize the resultant aqueous solution to obtain 1,3-N,N'-carbonyl-6'-N-acetylsisomicin.

2. In the foregoing procedure, by utilizing 1,3-N,N'-carbonyl-1-N-ethylsisomicin as starting material there is obtained 1,3-N,N'-carbonyl-6'-N-acetyl-1-N-ethylsisomicin.

B. 1,3-N,N'-carbonyl-6'-N-acetylaminoglycosides and 1,3-N,N'-carbonyl-6'-N-acetyl-1-N-ethylaminoglycosides 1. In a manner similar to that described in Preparation IIA1, treat with acetylimidazole the following 1,3-N,N'-carbonylaminoglycosides from Preparation IB1:

1,3-N,N'-carbonylgentamicin C$_{1a}$,
1,3-N,N'-carbonyltobramycin,
1,3-N,N'-carbonyl-Antibiotic 66-40B,
1,3-N,N'-carbonyl-Antibiotic 66-40D, 1,3-N,N'-carbonyl-Antibiotic JI-20A and the 5-epi, 5-epi-azido-5-deoxy and 5-epi-amino-5-deoxy analogs of the foregoing and of 1,3,-N,N'-carbonylsisomicin; and
1,3-N,N'-carbonyl-Antibiotic Mu-1,
1,3-N,N'-carbonyl-Antibiotic Mu-2,
1,3-N,N'-carbonyl-Antibiotic Mu-4 and
1,3-N,N'-carbonyl-Antibiotic Mu-5.

Isolate and purify each of the resultant products in a manner similar to that described to obtain the corresponding 1,3-N,N'-carbonyl-6'-N-acetylaminoglycoside.

2. In the procedure of Preparation IIAl, by utilizing as starting compounds the l-N-ethyl derivatives of the 1,3-N,N'-carbonylaminoglycosides of Preparation IIBl, there is obtained the corresponding 1,3-N,N'-carbonyl-6'-N-acetyl-l-N-ethylaminoglycosides.

C.
1,3-N,N'-Carbonyl-6'-N-acetyl-1-N-alkylaminoglycosides

In the procedure of Preparation IIAl, by utilizing the l-N-propyl and l-N-butyl derivatives of the 1,3-N,N'-carbonylaminoglycosides of Preparation IIBl, there is obtained the corresponding:

1,3-N,N'-carbonyl-6'-N-acetyl-l-N-propylaminoglycoside and
1,3-N,N'-carbonyl -6'-N-acetyl-l-N-butylaminoglycoside.

PREPARATION III

Preparation of Aldehyde Intermediates

A. S-γ-Acetamido-α-hydroxybutanal and the R-enantiomer thereof

1. Protect the amino function in S-γ-amino-α-hydroxy butyric acid by conversion thereof to an acetamido function; esterify the resultant S-γ-acetamido-α-hydroxybutyric acid with methanol; reduce the resultant S-γ-acetamido-α-hydroxybutyric acid methyl ester with di-isobutylaluninum hydride according to known procedures to obtain S-γ-acetamido-α-hydroxybutanal.

2. Treat R-γ-amino-α-hydroxybutyric acid in the manner described in Preparation IIIA(l) to obtain R-γ-acetamido-α-hydroxybutanal.

B. S-β-acetamido-α-hydroxypropanal and the R-enantiomer thereof

Treat each of S-β-amino-α-hydroxypropionic acid and R-β-amino-α-hydroxypropionic acid in the manner of Preparation IIIA1 to obtain S-β-acetamido-α-hydroxypropanal and R-β-acetamido-α-hydroxypropanal, respectively.

PREPARATION IV

6'-N-UNSUBSTITUTED-POLY-N-ACETYL-l-N-ETHYLAMINOGLYCOSIDES

A. 6'-N-Trifluoroacetyl-l-N-ethylaminoglycosides 1. 6'-N-trifluoroacetyl-l-N-ethylsisomicin Dissolve 47.8 gms. of 1-N-ethylsisomicin (100.6 mmoles) in 1100 ml. of methanol. Slowly add over a period of 10-30 minutes with stirring a solution of 13.5 ml. of ethyltrifluorothiolacetate (105 mmoles, 1.05 equivalents) in 75 ml. of methanol. Stir the solution at room temperature for an additional period of 1/2 to 2 hours, then evaporate in vacuo to a residue comprising 6' -N-trifluoroacetyl-l-N-ethylsisomicin, which is used without further purification in following Preparation IVBl.

2. In a manner similar to that described in Preparation IVAl, treat each of the following aminoglycosides with ethyltrifluorothiolacetate in methanol:

a. 1-N-ethylgentamicin $C_1$ a,
b. 1-N-ethylgentamicin B,
c. 1-N-ethyl-Antibiotic JI-20A,
d. 1-N-ethyl-Antibiotic 66-40B,
e. 1-N-ethyl-Antibiotic 66-40D,
f. 1-N-ethyltobramycin,
g. the 5-epi-, 5-epi-amino-5-deoxy, and the 5-epi-azido-5-deoxy-analogs of the foregoing and of 1-N-ethylsisomicin,
h. 1-N-ethyl-Antibiotic Mu-1,
i. 1-N-ethyl-Antibiotic Mu-2,
j. 1-N-ethyl-Antibiotic Mu-4, and
k. 1-N-ethyl-Antibiotic Mu-5.

Isolate each of the resulting products in a manner similar to that described hereinabove to obtain, respectively, a. 6'-N-trifluoroacetyl-1-N-ethylgentamicin $C_1$ a,
b. 6'-N-trifluoroacetyl-1-N-ethylgentamicin B,
c. 6'-N-trifluoroacetyl-1-N-ethyl-Antibiotic JI-20A,
d. 6'-N-trifluoroacetyl-1-N-ethyl-Antibiotic 66-40B,
e. 6'-N-trifluoroacetyl-1-ethyl-Antibiotic -66-40D,
f. 6'-N-trifluoroacetyl-1-N-ethyltobramycin,
g. the 5-epi-, 5-epi-amino-5-deoxy-, and the 5-epi-azido-5-deoxy-analogs of the foregoing and of 6'-N-trifluoroacetyl-1-N-ethylsisomicin
h. 6'-N-trifluoroacetyl-1-N-ethyl-Antibiotic Mu-1,
i. 6'-N-trifluoroacetyl-1-N-ethyl-Antibiotic Mu-2,
j. 6'-N-trifluoroacetyl-1-N-ethyl-Antibiotic Mu-4, and
k. 6'-N-trifluoroacetyl-1-N-ethyl-Antibiotic Mu-5.

B.
6'-N-Trifluoroacetyl-Poly-N-Acetyl-1-N-ethylaminoglycosides p 1. 1,3,2',
3"-tetra-N-acetyl-6'-N-trifluoroacetyl-1-N-ethylsisomicin Dissolve 6'-N-trifluoroacetyl-1-N-ethylsisomicin prepared as described in Preparation IVA1 in 900 ml. of methanol. Cool the solution to about −4° C, then add with stirring 67.5ml. of acetic anhydride (715 mmoles, 7.05 equivalents). Stir the solution at room temperature for a period of from about 2 to 18 hours until the reaction is complete as determined by thin layer chromatography. Evaporate the solution in vacuo to a residue comprising 1,3,2', 3"-tetra-N-acetyl-6'-N-trifluoroacetyl-1-N-ethylsisomicin. 2. In a manner similar to that described in Preparation IVB 1, treat each of the products obtained in Preparation IVA 2 (a-k) with acetic anhydride in methanol. Isolate and purify each of the resultant products in a manner similar to that described to obtain, respectively, a. 1,3,2',3"-tetra-N-acetyl-6'-N-trifluoroacetyl-1-N-ethyl-gentamicin $C_1$ a,
b. 1,3,3"-tri-N-acetyl-6'-N-trifluoroacetyl-1-N-ethyl-gentamicin B,
c. 1,3,2',3"-tetra-N-acetyl-6'-N-trifluoroacetyl-1-N-ethyl-Antibiotic JI-20A, d. 1,3,2',3"-tetra-N-acetyl-6'-N-trifluoroacetyl-1-N-ethyl-Antibiotic 66-40B,
e. 1,3,2',3"-tetra-N-acetyl-6'-N-trifluoroacetyl-1-N-ethyl-Antibiotic 66-40D,
f. 1,3,2',3"-tetra-N-acetyl-6'-N-trifluoroacetyl-1-N-ethyl-tobramycin,
g. the 5-epi-, 5-epi-N-acetylamino-5-deoxy-and 5-epi-azido-5-deoxy-analogs of the foregoing and of 1,3,2',3"-tetra-N-acetyl-6'-N-trifluoroacetyl-1-N-ethylsisomicin,
h. 1,3,2',3"-tetra-N-acetyl-6'-N-trifluoroacetyl-1-N-ethyl-Antibiotic Mu-1,
i. 1,3,2',3"-tetra-N-acetyl-6'-N-trifluoroacetyl-1-N-ethyl-Antibiotic Mu-2,
j. 1,3,2',3"-tetra-N-acetyl-6'-N-trifluoroacetyl-1-N-ethyl-Antibiotic Mu-4, and
k. 1,3,5,2',3"-penta-N-acetyl-6'-N-trifluoroacetyl-1-N-ethyl Antibiotic Mu-5;

C.
6'-N-Unsubstituted-Poly-N-Acetyl-1-N-ethylaminoglycosides 1. 1,3,2',3"-tetra-N-acetyl-1-N-ethylsisomicin Dissolve the 1,3,2',3"-tetra-N-acetyl-6'-N-trifluoroacetyl-1-N-ethylsisomicin prepared as described in Preparation IVB1 in methanol. Add 500 ml. of 28% aqueous ammonium hydroxide and allow the solution to stand at room temperature overnight. Evaporate the solution in vacuo to a residue comprising 1,3,2',3"-tetra-N-acetyl-1-N-ethylsisomicin. Purify by chromatographing on silica gel eluting with a solvent mixture comprising chloroform methanol1:14% ammonium hydroxide (27.7:6:1), taking 20 ml. fractions. Monitor the eluted fractions via thin layer chromatography on silica gel using the lower phase of chloroform:methanol:28% ammonium hydroxide (1:1:1) as developer. Combine like fractions and evaporate in vacuo to a residue of 1,3,2',3"-tetra-N-acetyl-1-N-ethylsisomicin.

2. In a manner similar to that described in Preparation IVC1, treat each of the 6'-N-trifluoroacetyl-poly-N-acetyl-1-N-ethylaminoglycosides of Preparation IVB2 (a-k) with aqueous ammonium hydroxide. Isolate and purify each of the resultant products in a manner similar to that described to obtain, respectively;

a. 1,3,2',3"-tetra-N-acetyl-1-N-ethylgentamicin C$_{1a}$,
b. 1,3"-tri-N-acetyl-1-N-ethylgentamicin B,
c. 1,3,2',3"-tetra-N-acetyl-1-N-ethyl-Antibiotic JI-20A,
d. 1,3,2',3"-tetra-N-acetyl-1-N-ethyl-Antibiotic 66-40B,
e. 1,3,2',3"-tetra-N-acetyl-1-N-ethyl-Antibiotic 66-40D,
f. 1,3,2',3"-tetra-N-acetyl-1-N-ethyltobramycin,
g. the 5-epi-, 5-epi-N-acetylamino-5-deoxy-, and 5-epi-azido-5-deoxy-analogs of the foregoing and of 1,3,2',3"-tetra-N-acetyl-1-N-acetylsisomicin,
h. 1,3,2',3"-tetra-N-acetyl-1-N-ethyl-Antibiotic Mu-1,
i. 1,3,2',3"-tetra-N-acetyl-1-N-ethyl-Antibiotic Mu-2,
j. 1,3,2',3"-tetra-N-acetyl-1-N-ethyl-Antibiotic Mu-4, and
k. 1,3,5,2',3"-penta-N-acetyl-1-N-ethyl-Antibiotic Mu-5.

2'-N-ALKYLAMINOGLYCOSIDES PREPARED FROM THE CORRESPONDING UNSUBSTITUTED AMINOGLYCOSIDES

EXAMPLE I

2'-N-Alkylsisomicin and 2'-N-Alkylverdamicin

A. 2'-N-Ethylsisomicin

To a solution of 5 gm. of sisomicin in 250 ml. of water, add 1N sulfuric acid until the pH of the solution is adjusted to about 5. To the solution of sisomicin sulfuric acid addition salt thereby formed, add 2 ml. of acetaldehyde, stir for 10 minutes, the add 0.85 gm. of sodium cyanoborohydride. Continue stirring at room temperature for 15 minutes, concentrate the solution in vacuo to a volume of about 100 ml. treat the solution with a basic ion exchange resin (e.g. Amberlite IRA 401S (OH-)), the lyophilize to a residue comprising 2'-N-ethylsisomicin.

Purify by chromatographing on 200 gm. of silica gel, eluting with the lower phase of a chloroform-methaol-7% ammonium hydroxide (2:1:1) system. Combine like eluates as determined by thin layer chromatography. Concentrate in vacuo the combined eluates of the 2'-N-ethylsisomicin component as determined by nmr and mass spectral data. Further purify the resultant residue by again chromatographing on 100 gm. of silica gel eluting with a chloroform-methanol-3.5% ammonium hydroxide (1:2:1) system. Pass the combined, like eluates (as determined by thin layer chromatography) through a column of basic ion exchange resin and lyophilize the eluate to obtain 2'-N-ethylsisomicin. $[\alpha]_D^{26°}$ + 160.2° (0.3%, H$_2$O); pmr (ppm) (D$_2$O): δ 1.00 (3H, t, J=7.0 Hz, CH$_3$-CH$_2$); 1.15 (3H, s, CH$_3$-C); 2.46 (3H, s, CH$_3$-N); 3.75 (1H, dd, J=4.0 Hz, 10.0 Hz, H$_2$"); 4.0 (1H, d, J=12 Hz, H$_5$"e); 4.85 (1H, m, C=CH); 5.02 (1H, d, J=4.0 Hz, H$_1$"); 5.45 (1H, d, J=2.0 Hz, H$_1$');

Mass spectrum: (M + 1) + m/e 475
also m/e 145, 155, 160, 163, 173, 191, 284, 289, 299, 304, 317, 322, 332, 345, 350, 390, 430.

B. 2'-N-Propylsisomicin

In a manner similar to that described in Example IA, treat the sulfuric acid addition salt of sisomicin in water with propanol and sodium cyanoborohydride. Isolate and purify the resultant product in a manner similar to that described, to obtain 2'-N-propylsisomicin;
$[\alpha]_D^{26°}$ + 134.6° (0.3%, H$_2$O)

Mass Spectrum: (M + 1) + m/e 489
also m/e 145, 160, 163, 169, 298, 304, 313, 322, 331, 332, 359, 404.

C. 2'-N-Butylsisomicin

In a manner similar to that described in Example IA, treat the sulfuric acid addition salt of sisomicin in water with butanal and sodium cyanoborohydride. Isolate and purify the resultant product in a manner similar to that described to obtain 2'-N-butylsisomicin.
$[\alpha]_D^{26°}$ + 153.3° (H$_2$O); pmr (ppm) (D$_2$O); δ 0.85 (3H, t, J=7.0 Hz, CH$_3$-CH$_2$); 1.15 (3H, s, CH$_3$-C), 2.48 (3H, s, CH$_3$-N); 3.75 (1H, dd J=4.0 Hz, 10 Hz, H$_2$"); 4.05 (1H, d, J=12 Hz, H$_5$"e); 4.85 (1H, m, C=CH); 5.06 (1H, d, J=4.0Hz, H$_1$"); 5.49 (1H, d, J=2.0 Hz, H$_1$'):
Mass Spectrum: (M + 1) + m/e 503
also m/e 145, 160, 163, 173, 183, 191, 304, 312, 327, 332, 345, 373, 418.

D. 2'-N-(δ-aminobutyl)sisomicin

Add 1N sulfuric acid dropwise to a solution of 3 gm. of sisomicin in 120 ml. of water until the pH of the solution is adjusted to about 5. To the aqueous solution of the sulfuric acid addition salt of sisomicin thereby formed, add 6 gm. of γ-acetamidobutanal. Continue stirring for 10 minutes the add 600 mg. of sodium cyanoborohydride. After 2 hours concentrate the solution to a small volume and pour into 1 liter of anhydrous ethanol with stirring and collect by filtration the resultant precipitate, dissolve in water and pass the aqueous solution through a column of Amberlite IRA 401-S L (OH−) ion exchange resin. Evaporate the eluate and chromatograph the resultant residue on silica gel eluting with the lower phase of a chloroformmethanol-7% aqueous ammonium hydroxide solvent mixture. Evaporate the combined, like eluates to a residue comprising 2'-N-(δ-acetamidobutyl)sisomicin.

Treat 2'-N-(δ-acetamidobutyl)sisomicin with 10% aqueous potassium hydroxide and heat at 100° C for 3 hours, then neutralize with Amberlite IRC-50 ion exchange resin and elute with 2N aqueous hydroxide. Concentrate the eluant and dissolve the resultant residue in water and lyophilize to obtain 2'-N-(δ-aminobuty)sisomicin.

E. 2'-N-(δ-aminopropyl)sisomicin

In a manner similar to that described in Example ID, treat the sulfuric acid addition salt of sisomicin in water with β-acetamidopropanal and sodium cyanoborohydride. Isolate and purify the resultant product in a similar manner to that described to obtain 2'-N-(δ-aminoprop yl)sisomicin.

F. 2'-N-Butylverdamicin

In a manner similar to that described in Example IA, treat the sulfuric acid addition salt of verdamicin in water with butanal and sodium cyanoborohydride. Isolate, and purify the resultant product in a manner similar to that described to obtain 2'-N-butylverdamicin.
$[\alpha]_D^{26°}$ + 137.7° (0.3%, $H_2O$);
Mass spectrum: (M + 1) + m/e 517
also m/e 145, 160, 163, 191, 197, 289, 304, 322, 326, 332, 341, 359, 387, 418, 500.

EXAMPLE II

2'-N-Alkylaminoglycosides

A. In a manner similar to that described in Example IA, treat the sulfuric acid addition salts of the following aminoglycosides with each of acetaldehyde, propanal, and butanal together with sodium cyanoborohydride:

Gentamicin A,
Gentamicin $C_1a$,
Gentamicin $C_2$,
Gentamicin $C_2a$,
Gentamicin $X_2$,
Verdamicin,
Tobramycin,
Antibiotic G-148,
Antibiotic 66-40B,
Antibiotic 66-40D,
Antibiotic JI-20A,
Antibiotic JI-20B, the 5-epi, 5-epi-azido-5-deoxy, 5-epi-amino-5-deoxy analogs of the foregoing and of sisomicin;
and Antibiotic Mu-1, Antibiotic Mu-2, Antibiotic Mu-4, and Antibiotic Mu-5.

Isolate and purify each of the resultant products in a manner similar to that described to obtain the corresponding 2'-N-ethyl, 2'-N-propyl or 2'-N-butylaminoglycoside.

B. In a manner similar to that described in Example ID, treat the sulfuric acid addition salts of the aminoglycosides of Example IIA with each of β-acetamidopropanal of γ-acetamidobutana together with sodium cyanoborohydride.

Isolate and purify each of the resultant products in a manner similar to that described to obtain the corresponding 2'-N-(γ-aminopropyl)- or 2'-N-(δ-aminobutyl)aminoglycoside.

PREPARATION OF 1,3-N,N'-CARBONYL DERIVATIVES OF 2'-N-ALKYL AND 1,2'-DI-N-ALKYLAMINOGLYCOSIDES

EXAMPLE III

1,3-N,N'-Carbonyl-2'-N-Alkylaminoglycosides and 1,3-N,N'-Carbonyl-2'-N-alkyl-1-N-ethylaminoglycosides A. 1,3-N,N'-carbonyl-2'-N-ethylsisomicin and 1,3-N,N'-carbonyl-1,2'-di-N-ethylsisomicin 1. To a solution of 1.1 gms. of 1,3-N,N'-carbonylsisomicin from Preparation IA1 in 30 ml. of 25% aqueous methanol, add 1N sulfuric acid until the pH is between 5 and 6. Add 0.3 ml. acetaldehyde and 120 mg. sodium cyanoborohydride. Stir for 30 minutes and then concentrate to a residue comprising 1,3-N,N'-carbonyl-2'-ethylsisomicin.

2. In the foregoing procedure, by utilizing 1,3-N,N'-carbonyl-1-N-ethylsisomicin from Preparation IA2 as starting compound, there is obtained 1,3-N,N'-carbonyl-1,2'-di-N-ethylsisomicin.

B. 1,3-N,N'-carbonyl-2'-N-alkylsisomicin and 1,3-N,N'-carbonyl-2'-N-alkyl-1-N-ethylsisomicin 1. In the procedure of Example IIIA1, instead of acetaldehyde, substitute equivalent amounts of the following adehydes:

1. propanal
2. butanal
3. 2-ethylbutanal
4. n-octanal,
5. propenal,
6. phenylacetaldehyde,
7. cyclohexanecarboxaldehyde,
8. benzaldehyde,
9. hydroxyacetaldehyde, and
10. 2-hydroxypropanal.

Isolate and purify each of the resultant products in a manner similar to that described in Example IIIA1 to obtain, respectively:

1. 1,3-N,N'-carbonyl-2'-N-propylsisomicin,
2. 1,3-N,N'-carbonyl-2'-N-butylsisomicin,
3. 1,3-N,N'-carbonyl-2'-N-(β-ethylbutyl)-sisomicin,
4. 1,3-N,N'-carbonyl-2'-N-(n-octyl)-sisomicin,
5. 1,3-N,N'-carbonyl-2'-N-(β-propenyl)sisomicin,
6. 1,3-N,N'-carbonyl-2'-N-phenylethylsisomicin, 7. 1,3-N,N'-carbonyl-2'-N-cyclohexylmethylsisomicin,
8. 1,3-N,N'-carbonyl-2'-N-benzylsisomicin,
9. 1,3-N,N'-carbonyl-2'-N-(β-hydroxyethyl)sisomicin, and
10. 1,3-N,N'-carbonyl-2'-N-(β-hydroxypropyl)sisomicin.

2. In the foregoing procedure, by utilizing 1,3-N,N'-carbonyl-1-N-ethylsisomicin as starting compound and equivalent amounts of the aldehydes of Example IIIB1 (1-10) there is obtained respectively:

1. 1,3-N,N'-carbonyl-2'-N-propyl-1-N-ethylsisomicin,
2. 1,3-N,N'-carbonyl-2'-N-butyl-1-N-ethylsisomicin,
3. 1,3-N,N'-carbonyl-2'-N-(β-ethylbutyl)-1-N-ethylsisomicin,
4. 1,3-N,N'-carbonyl-2'-N-(n-octyl)-1-N-ethylsisomicin,
5. 1,3-N,N'-carbonyl-2'-N-(β-propenyl)-1-N-ethylsisomicin,
6. 1,3-N,N'-carbonyl-2'-N-phenylethyl-1-N-ethylsisomicin,
7. 1,3-N,N'-carbonyl-2'-N-cyclohexylmethyl-1-N-ethylsisomicin,
8. 1,3-N,N'-carbonyl-2'-N-benzyl-1-N-ethylsisomicin,
9. 1,3-N,N'-carbonyl-2'-N-(β-hydroxyethyl)-1-N-ethylsisomicin,
10. 1,3-N,N'-carbonyl-2'-N-(β-hydroxypropyl)-1-N-ethylsisomicin.

C. 1,3-N,N'-Carbonyl-2'-N-(aminoalkyl)sisomicin, 1,3-N,N'-carbonyl-2'-N-(aminoalkyl)-1-N-ethylsisomicin and
1,3-N,N'-Carbonyl-2'-N-(Hydroxyaminoalkyl)sisomicin and
1,3-N,N'-carbonyl-2'-N-(hydroxyaminoalkyl)-1-N-ethylsisomicin 1. In a manner similar to that described in Example IIIA1, treat the sulfuric acid addition salt of 1,3-N,N'-carbonylsisomicin in aqueous methanol with sodium cyanoborohydride and with each of the following amino substituted aldehydes:

1. β-acetamidopropanal
2. γ-acetamidobutanal
3. phthalimidoacetaldehyde
4. S-γ-acetamido-α-hydroxybutanal
5. R-γ-acetamido-α-hydroxybutanal
6. S-β-acetamido-α-hydroxypropanal and
7. S-β-acetamido-α-hydroxypropanal.

Isolate and purify each of the resultant products in a manner similar to that described to obtain, respectively:

1. 1,3-N,N'-carbonyl-2'-N-(γ-acetamidopropyl)sisomicin,
2. 1,3-N,N'-carbonyl-2'-N-(δ-acetamidobutyl)sisomicin,
3. 1,3-N,N'-carbonyl-2'-N-(β-phthalimidoethyl)sisomicin,
4. 1,3-N,N'-carbonyl-2'-N-(S-δ-acetamido-β-hydroxybutyl)sisomicin,
5. 1,3-N,N'-carbonyl-2'-N-(R-δ-acetamido-β-hydroxybutyl)sisomicin,
6. 1,3-N,N'-carbonyl-2'-N-(S-γ-acetamido-β-hydroxypropyl)sisomicin,
7. 1,3-N,N'-carbonyl-2'-N-(R-γ-acetamido-β-hydroxypropyl)sisomicin.

2. In the foregoing procedure, by utilizing 1,3-N,N'-carbonyl-1-N-ethylsisomicin as the starting compound and equivalent amounts of the amino substituted aldehydes of Example IIIC1 (1-7), there is obtained respectively:

1. 1,3-N,N'-carbonyl-2'-N-(γ-acetamidopropyl)-1-N-ethylsisomicin,
2. 1,3-N,N'-carbonyl-2'-N-(δ-acetamidobutyl)-1-N-ethylsisomicin,
3. 1,3-N,N'-carbonyl-2'-N-(β-phthalimidoethyl)-1-N-ethylsisomicin,
4. 1,3-N,N'-carbonyl-2'-N-(S-δ-acetamido-β-hydroxybutyl)-1-N-ethylsisomicin,
5. 1,3-N,N'-carbonyl-2'-N-(R-δ-acetamido-β-hydroxybutyl)-1-N-ethylsisomicin,
6. 1,3-N,N'-carbonyl-2'-N-(S-γ-acetamido-β-hydroxypropyl)-1-N-ethylsisomicin,
7. 1,3-N,N'-carbonyl-2'-N-(R-γacetamido-β-hydroxypropyl)-1-N-ethylsisomicin.

D. 1,3-N,N'-Carbonyl-2'-N-ethylaminoglycosides and 1,3-N,N'-carbonyl-1,2'-di-N-ethylaminoglycosides 1. In a manner similar to that described in Example IIIA1, treat the 1,3-N,N'-carbonylaminoglycosides of Preparation IB1 with sulfuric acid, acetaldehyde and sodium cyanoborohydride. Isolate in a similar manner to obtain the corresponding 1,3-N,N'-carbonyl-2'-N-ethylaminoglycosides.

2. In the foregoing procedure by utilizing a 1,3-N,N'-carbonyl-1-N-ethylaminoglycoside from Preparation IB2 as the starting material, there is obtained the corresponding 1,3-N,N'-carbonyl-1,2'-di-N-ethylaminoglycoside.

E. 1,3-N,N'-Carbonyl-2'-N-Alkylaminoglycosides and 1,3-N,N'-carbonyl-2'-N-alkyl-1-N-alkylaminoglycoside 1. In a manner similar to that described in Example IIIA1, treat the 1,3-N,N'-carbonylaminoglycosides of Preparation IB1 with sulfuric acid, and with each of the aldehyde reagents of Example IIIB1 (1-10) and IIIC1 (1-7) and with sodium cyanoborohydride. Isolate in a similar manner to obtain the corresponding 1,3-N,N'-carbonyl-2'-N-alkylaminoglycoside derivatives.

2. In the foregoing procedure, by utilizing a 1,3-N,N'-carbonyl-1-N-alkylaminoglycoside of Preparation IC as starting compound and the aldehyde reagents of Example IIIB1 (1-10) and IIIC1 (1-7) there is obtained the corresponding 1,3-N,N'-carbonyl-2'-N-(alkyl or aminoalkyl or hydroxyaminoalkyl)-1-N-alkylaminoglycoside.

EXAMPLE IV 1,3-N,N'-Carbonyl-2'-N-Alkyl-6'-N-Acetylsisomicin and
1,3-N,N'-Carbonyl-2'-N-Alkyl-6'-N-Acetyl-1-N-ethylsisomicin A. 1,3-N,N'-carbonyl-2'-N-ethyl-6'-N-acetylsisomicin and
1,3-N,N'-carbonyl-1,2'-di-N-ethyl-6'-N-acetylsisomicin 1. To a solution of 1.1 gm. of 1,3-N,N'-carbonyl-6'-N-acetylsisomicin of Preparation IIA1 in 30 ml. of 25% aqueous methanol, add 1N sulfuric acid until the pH is between 5 and 6, followed by 0.3 ml. of acetaldehyde and 120 mg. of sodium cyanoborohydride. Stir for 30 minutes, then evaporate in vacuo to a residue comprising 1,3-N,N'-carbonyl-2'-N-ethyl-6'-N-acetylsisomicin.

2. In the foregoing procedure by utilizing as starting compound 1,3-N,N'-carbonyl-6'-N-acetyl-1-N-ethylsisomicin from Preparation IIA2, there is obtained the corresponding 1,3-N,N'-carbonyl-1,2'-di-N-ethyl-6'-N-acetylsisomicin.

B. 1,3-N,N'-Carbonyl-2'-N-alkyl-6'-N-acetylaminoglycosides and 1,3-N,N'-carbonyl-2'-N-alkyl-6'-N-acetyl-1-N-alkylaminoglycosides 1. In a manner similar to that described in Example IVA1, treat each of the 1,3-N,N'-carbonyl-6'-N-acetylaminoglycosides of Preparation IIB1 with sulfuric acid and each of the aldehyde reagents listed in Example IIIB1 (1-10) and IIIC1 (1-7) and with sodium cyanoborohydride to obtain the corresponding 1,3-N,N'-carbonyl-2-N-(alkyl or aminoalkyl or hydroxyaminoalkyl)-6'-N-acetylaminoglycoside derivatives.

2. In the foregoing procedure treat the 1,3-N,N'-carbonyl-6'-N-acetyl-1-N-alkylaminoglycosides of Preparation IIC with each of the aldehydes of Example IIIB1 (1-10) and IIIC1 (1-7) to obtain the corresponding 1,3-N,N'-carbonyl-2'-N-(alkyl or aminoalkyl or hydroxyaminoalkyl)-6'-N-acetyl-1-N-alkylaminoglycoside derivatives.

EXAMPLE V

2'-N-Alkylaminoglycosides Prepared From the 1,3-Carbonyl Derivatives

A. 2'-N-ethylsisomicin

Dissolve 1,3-N,N'-carbonyl-2'-N-ethyl-6'-N-acetylsisomicin of Example IVA1 or 1,3-N,N'-carbonyl-2'-N-ethylsisomicin of Example IIIA1 in 90% aqueous hydrazine and heat in an atmosphere of nitrogen at 110° C for 48 hours. Remove the solvent by evaporation and chromatograph the residue on silica gel in the lower phase of a chloroform, methanol, 10% aqueous ammonium hydroxide (2:1:1) solvent mixture. Monitor the eluates by thin layer chromatography and combine and evaporate to a residue to obtain 2'-N-ethylsisomicin.

B. 2'-N-alkylsisomicins

In a manner similar to that described in Example VA, treat each of the 1,3-N,N'-carbonyl-2'-N-alkyl derivatives prepared in Examples IIIB1 (1-10) and III C1 (1-7) with hydrazine. Isolate each of the resulting products in a manner similar to that described to obtain, respectively:

1. 2'-N-propylsisomicin,
2. 2'-N-butylsisomicin,
3. 2'-N-($\beta$-ethylpropyl)sisomicin,
4. 2'-N-(n-octyl)sisomicin,
5. 2'-N-($\beta$-propenyl)sisomicin,
6. 2'-N-phenylethylsisomicin,
7. 2'-N-cyclohexylmethylsisomicin,
8. 2'-N-benzylsisomicin,
9. 2'-N-($\beta$-hydroxyethyl)sisomicin,
10. 2'-N-($\beta$-hydroxypropyl)sisomicin,
11. 2'-N-($\gamma$-aminopropyl)sisomicin,
12. 2'-N-($\delta$-aminobutyl)sisomicin,
13. 2'-N-($\beta$-aminoethyl)sisomicin,
14. 2'-N-(S-$\delta$-amino-$\beta$-hydroxybutyl)sisomicin,
15. 2'-N-(R-$\delta$-amino-$\beta$-hydroxybutyl)sisomicin,
16. 2'-N-(S-$\gamma$-amino-$\beta$-hydroxypropyl)sisomicin, and
17. 2'-N-(R-$\gamma$-amino-$\beta$-hydroxypropyl)sisomicin.

C. 2'-N-alkylaminoglycosides

In a manner similar to that described in Example VA, react with hydrazine, each of the following:

1. 1,3-N,N'-carbonyl-2'-N-ethylaminoglycoside of Example IIID1,
2. 1,3-N,N'-carbonyl-2'-N-alkylaminoglycosides of Example IIIE1, and,
3. the 1,3-N,N'-carbonyl-2'-N-alkyl-6'-N-acetylaminoglycosides of Example IVB 1.

Isolate and purify each of the resultant products in a manner similar to that described to obtain the corresponding 2'-N-alkylaminoglycosides.

EXAMPLE VI 1,2'-Di-N-Ethylsisomicin; 1,2'-Di-N-Ethylaminoglycosides, 1,2'-Di-N-Alkylsisomicin and 1,2'-Di-N-Alkylaminoglycosides Prepared from the Corresponding Unsubstituted Aminoglycosides

A. 1,2'-di-N-ethylsisomicin

1. In an atmosphere of nitrogen, to a solution of 100 gm. of sisomicin in 2.5 liters of distilled water at about 4° C, add 1N sulfuric acid until the pH of the solution is adjusted to about 2.5. To the solution of sisomicin sulfuric acid addition salt thereby formed, add 30 ml. of chilled acetaldehyde, stir for 10 minutes, then over a period of 20 minutes add a solution of 4.5 gm. sodium cyanoborohydride in 120 ml. of distilled water keeping the pH below 3.5 by further addition of 1N sulfuric acid. Continue stirring for 20 minutes, concentrate the solution in vacuo to about 1 liter, adjust the pH to about 11 with 1N NaOH and then continue the concentration in vacuo to a residue. Extract the residue with methanol, combine the extracts, filter and reduce to a residue comprising 1,2'-di-N-ethylsisomicin.

Purify by chromatographing on silica gel, eluting with the lower phase of a chloroform-isopropanol-21% ammonium hydroxide system (2:1:1). Combine like eluates as determined by thin layer chromatography. Concentrate in vacuo the combined eluates of the 1,2'-di-N-ethylsisomicin component as determined by nmr and mass spectral data and lyophilize to obtain 1,2'-di-N-ethylsisomicin.

$[\alpha]_D^{26°}$ + 131.6°(0.3%, H$_2$O); pmr (ppm) (D$_2$O)$\delta$ 1.03 (6H, t, J=7Hz, CH$_3$-CH$_2$); 1.18 (3H, s, C-CH$_3$); 2.50 (3H, s, NCH$_3$); 3.78 (1H, dd, J=4Hz, 10Hz, H$_2$"); 4.02 (1H, d, J=12Hz, H$_5$"e); 4.85 (1H, m, C=CH); 4.96 (1H, d, J=4Hz, H$_1$"); 5.46 (1H, d, J=2.5Hz, H$_1$');

Mass Spectrum: (M + 1)+ m/e 504
also 155, 160, 173, 191, 201, 219, 284, 327, 332, 345, 350, 360, 373, 418, 503.

2. In the procedure of Example VIA 1, by utilizing as starting compound the sulfuric acid addition salt of the 1-N-ethyl or 2'-N-ethyl derivative of sisomicin, there is obtained 1,2'-di-N-ethylsisomicin.

B. 1,2'-di-N-ethylaminoglycosides

In the procedure of Example VIA 1, utilize as starting compounds the sulfuric acid addition salts of the following aminoglycosides or the 1-N-ethyl or 2'-N-ethyl derivatives thereof:

Gentamicin A
Gentamicin C$_{1a}$,
Gentamicin C$_2$,

Gentamicin $C_{2a}$,
Gentamicin $X_2$,
Verdamicin,
Tobramycin,
Antibiotic G-418
Antibiotic 66-40B,
Antibiotic 66-40D,
Antibiotic JI-20A,
Antibiotic JI-20B, The 5-epi, 5-epi-azido-5-deoxy, 5-epi-amino-5-deoxy analogs of the foregoing and of sisomicin; and Antibiotic Mu-1,
Antibiotic Mu-2,
Antibiotic Mu-4,
Antibiotic-Mu-5,
to obtain the corresponding 1,2'-di-N-ethylaminoglycosides.

C. 1,2'-di-N-alkylsisomicin

1. In the procedure of Example VIA 1, instead of acetaldehyde substitute an equivalent amount of propanal or butanal to treat the sulfuric acid addition salt of sisomicin to obtain respectively; 1,2'-di-N-propylsisomicin or 1,2'-di-N-butylsisomicin.

2. Alternatively, in the foregoing procedure, by reacting the sulfuric acid addition salts of 1-N-propylsisomicin or 2'-N-propylsisomicin with propanal, there is obtained 1,2'-di-N-propylsisomicin. Similarly, by reacting the sulfuric acid addition salt of 1-N-butylsisomicin or 2'-N-butylsisomicin with butanal, there is obtained 1,2'-di-N-butylsisomicin.

D. 1,2'-di-N-alkylaminoglycosides

1. In the procedure of Example VIA 1, instead of acetaldehyde substitute an equivalent amount of propanal or butanal to treat the sulfuric acid addition salts of the aminoglycosides of Example VIB to obtain the corresponding 1,2'-di-N-propylaminoglycoside or 1,2'-di-N-butylaminoglycoside.

2. Alternatively, in the foregoing procedure by reacting the 1-N-propyl or 2'-N-propyl derivatives of the sulfuric acid addition salts of the aminoglycoside of Example VIB with propanal, there is obtained the corresponding 1,2'-di-N-propylaminoglycoside. Similarly, by reacting the 1-N-butyl or 2'-N-butyl derivatives of the sulfuric acid addition salts of the aminoglycosides of Example VIB with butanal, there is obtained the corresponding 1,2'-di-N-butylaminoglycoside.

E. In the procedures of Example VIA-1, by doubling the quantity of cyanoborohydride used, greater yields are obtained of the 1,2'-di-N-alkylsisomicin thereby formed.

EXAMPLE VII 1,2'-di-N-alkylaminoglycosides prepared from the 1,3-carbonyl derivatives

A. 1,2'-di-N-ethylsisomicin

Dissolve 1,3-N,N'-carbonyl-1,2'-di-N-ethylsisomicin of Example IIIA-2 or 1,3-N,N'-carbonyl-1,2'-di-N-ethyl-6'-N-acetylsisomicin of Example IVA-2 in 90% aqueous hydrazine and heat in an atmosphere of nitrogen at 110° C for 48 hours. Remove the solvent by evaporation and chromatograph the residue on silica gel in the lower phase of a chloroform-isopropanol-21% ammonium hydroxide system (2:1:1). Combine like eluates as determined by thin layer chromatography. Concentrate in vacuo the combined eluates of 1,2'-di-N-ethylsisomicin as determined by nmr and mass spectral data and lyophilize to obtain 1,2'-di-N-ethylsisomicin.

B. 1,2'-di-N-ethylaminoglycosides

In the procedure of Example VIIA, by utilizing as starting compounds the 1,3-N,N'-carbonyl-1,2'-di-N-ethylaminoglycosides of Example IIID-2 there is obtained the corresponding 1,2'-di-N-ethylaminoglycoside.

C. 1-N-ethyl-2'-N-(alkyl) or aminoalkyl or hydroxyaminoalkyl) sisomicins

In the procedure of Example VIIA, by utilizing as starting compounds the 1,3-N,N'-carbonyl-2'-N-alkyl-1-N-ethylsisomicins of Example IIIB-2 (1–10) and the 1,3-N,N'-carbonyl-2'-N-(aminoalkyl or hydroxyaminoalkyl)-1-N-ethylsisomicins of Example IIIC2 (1–7) there is obtained the following:

1. 1-N-ethyl-2'-N-propylsisomicin,
2. 1-N-ethyl-2'-N-butylsisomicin,
3. 1-N-ethyl-2'-N-(β-ethylpropyl)sisomicin,
4. 1-N-ethyl-2'-N-(n-octyl)sisomicin,
5. 1-N-ethyl-2'-N-(β-propenyl)sisomicin,
6. 1-N-ethyl-2'-N-phenylethylsisomicin,
7. 1-N-ethyl-2'-N-cyclohexylmethylsisomicin,
8. 1-N-ethyl-2'-N-benzylsisomicin,
9. 1-N-ethyl-2'-N-(β-hydroxyethyl)sisomicin,
10. 1-N-ethyl-2'-N-(β-hydroxypropyl)sisomicin,
11. 1-N-ethyl-2'-N-(γ-aminopropyl)sisomicin,
12. 1-N-ethyl-2'-N-(δ-aminobutyl)sisomicin,
13. 1-N-ethyl-2'-N-(β-aminoethyl)sisomicin,
14. 1-N-ethyl-2'-N-(S-δ-amino-β-hydroxybutyl)sisomicin,
15. 1-N-ethyl-2'-N-(R-δ-amino-β-hydroxybutyl)sisomicin,
16. 1-N-ethyl-2'-N-(S-δ-amino-β-hydroxypropyl)sisomicin,
17. 1-N-ethyl-2'-N-(R-γ-amino-β-hydroxypropyl)sisomicin.

D. 1,2'Di-N-alkylaminoglycosides

In the procedure of Example VIIA, by utilizing as starting compounds the 1,3-N,N'-carbonyl-2'-N-(alkyl or aminoalkyl or hydroxyaminoalkyl)-1-N-alkylaminoglycosides of Example IIIE2 and the 1,3-N,N'-carbonyl-2'-N-(alkyl or aminoalkyl or hydroxyaminoalkyl)-6'-N-acetyl-1-alkylaminoglycosides of Example IVB2 there is obtained the corresponding 1-N-alkyl-2'-N-(alkyl or aminoalkyl or hydroxyaminoalkyl)aminoglycosides.

PREPARATION OF 1,6'-DI-N-ALKYLAMINOGLYCOSIDES FROM THE CORRESPONDING UNSUBSTITUTED AMINOGLYCOSIDES

EXAMPLE VIII 1,6'-Di-N-Ethylsisomicin, 1,6'-di-N-ethylaminoglycosides 1,6'-di-N-(alkyl or aminoalkyl)sisomocin, 1,6'-di-N-(alkyl or aminoalkyl) aminoglycosides

A. 1,6'-Di-N-Ethylsisomicin

1. In an atmosphere of nitrogen, to a solution of 100 gms. of sisomicin in 2.5 liters of water chilled to about 4° C — add dilute (1N) sulfuric acid to a pH of about 2.5. Then add 30 ml. of chilled acetaldehyde and stir for 15 minutes. Then over a 20 minute period add a solution of 4.5 gms. sodium cyanoborohydride in 120 ml. water, keeping the pH below 3.5 by the addition of dilute sulfuic acid.

Stir for 20 minutes and then concentrate in vacuo to about 1 liter, adjust the pH to 11 with 1N NaOH. Remove the remainder of the solvent in vacuo. Extract the residue with methanol, combine the methanol extracts, filter and reduce to dryness. Chromatograph the residue on silica gel in the lower phase of a chloroform-isopropanol-21% ammonium hydroxide system (2:1:1). Combine like eluates as determined by thin layer chromatography. Concentrate in vacuo the combined eluates of 1,6'-di-N-ethylsisomicin component as determined by nmr and mass spectral data. Lyophilize to obtain the 1,6'-di-N-ethylsisomicin.

$[\alpha]_D^{26°}$ + 131.5°(0.3%, H$_2$O); pmr (ppm) (D$_2$O)$\delta$ 1.00 (3H, t, 7.0Hz, CH$_3$-CH$_2$); 1.02 (3H, t, J=7Hz, CH$_2$-CH$_3$); 1.16 (3H, s, CH$_3$-C); 2.47 (3H, s, CH$_3$-N); 3.76 (1H, dd, J=10Hz, 4Hz, H$_2$''); 3.97 (1H, d, J=12Hz, H$_5$''e); 4.84 (1H, m, C=CH); 4.93 (1H, d, J=4Hz, H$_1$''); 5.28 (1H, d, J=2.0Hz, H$_1$')

Mass spectrum: (M + 1)+m/e 504
also m/e 155, 160, 173, 191, 201, 219, 284, 327, 332, 345, 350, 360, 373, 390, 503.

2. In the procedure of Example VIIIA 1, by utilizing as starting compound the sulfuric acid addition salts of the 1-N-ethyl or 6'-N-ethyl derivative of sisomicin, there is obtained 1,6'-di-N-ethylsisomicin.

B. 1,6'-di-N-ethylaminoglycosides

In the procedure of Example VIIIA1, utilize as starting compounds the sulfuric acid addition salts of the following aminoglycosides or the 1-N-ethyl or 6'-N-ethyl derivatives thereof:

Gentamicin B,
Gentamicin B$_1$,
Gentamicin C$_1$a,
Gentamicin C$_2$,
Gentamicin C$_2$a,
Verdamicin,
Tobramycin,
Antibiotic 66-40B,
Antibiotic66-40D,
Antibiotic JI-20A,
Antibiotic JI-20B, The 5-epi, 5epi-azido-5-deoxy, 5epi-amino-5deoxy analogs of the foregoing and of sisomicin; and Antibiotic Mu-1,
Antibiotic Mu-2,
Antibiotic Mu-4 and
Antibiotic Mu-5 to obtain the corresponding 1,6'-di-N-ethylaminoglycoside.

C. 1,6'-di-N-alkylsisomicin

1. In the procedure of Example VIIIA 1, ;l instead of acetaldehyde substitute an equivalent amount of propanal or butanal to obtain, respectively, 1,6'-di-N-propyl-sisomicin or 1,6'-di-N-butylsisomicin.

2. Alternatively, in the foregoing procedure by reacting the sulfuric acid addition salt of 1-N-propylsisomicin or 6'-N-propylsisomicin with propanal, there is obtained 1,6'-di-N-propylsisomicin. Similarly, by reacting the sulfuric acid addition salt of 1-N-butylsisomicin or 6'-N-butylsisomicin with butanal there is obtained 1,6'-di-N-butylsisomicin.

D. 1,6'-di-N-alkylaminoglycosides

1. In the manner of Example VIIIA1, but instead of acetaldehyde substitute an equivalent amount of propanal or butanal, treat the sulfuric acid addition salts of the aminoglycosides of Example VIIIB to obtain the corresponding 1,6'-di-N-propyl-aminoglycoside or 1,6'-di-N-butylaminoglycoside.

2. Alternatively, in the foregoing procedure, by reacting the sulfuric acid addition salt of the 1-N-propyl or 6'-N-propyl derivatives of the aminoglycosides of Example VIIIB with propanal, there is obtained the corresponding 1,6'-di-N-propylaminoglycoside. Similarly, by reacting the sulfunic acid addition salt of the 1-N-butyl or 6'-N-butyl derivatives of the aminoglycosides of Example VIIIB with butanal, there is obtained the corresponding 1,6'-di-N-butylaminoglycoside.

E. 1,6'-di-N-aminoalkylsisomicin

1. In the procedure of Example VIIIAI instead of acetaldehyde substitute an equivalent amount of $\beta$-acetamidopropanal or $\gamma$-acetamidobutanal to obtain the corresponding 1,6'-di-N-($\gamma$-acetamidopropyl)sisomicin or 1,6'-di-N-($\delta$-acetamidobutyl)sisomicin.

Treat the 1,6'-di-N-($\gamma$-acetamidopropyl)sisomicin or 1,6'-di-N-($\delta$-acetamidobutyl)sisomicin with 10% aqueous potassium hydroxide, heat for 3 hours, then neutralize with Amberlite IRC-50 ion exchange resin and elute with 2N aqueous ammonium hydroxide. Concentrate the eluate and dissolve the resultant residue in water to obtain 1,6'-di-N-($\gamma$-aminopropyl)sisomicin or 1,6'-di-N-($\delta$-aminobutyl)sisomicin, respectively.

2. Alternatively, in the foregoing procedure by reacting the sulfuric acid addition salt 1-N-($\gamma$-acetamidopropyl) or 6'-N-($\delta$-acetamidopropyl) derivatives of sisomicin with $\beta$-acetamido-propanal, there is obtained the corresponding 1,6'-di-N-($\gamma$-amino-propyl)sisomicin. Similarly, by reacting of the sulfuric acid addition salt of the 1-N-($\delta$-acetamidobutyl) or 6'-N-($\delta$-acetamido-butyl) derivatives of sisomicin with $\gamma$-acetamidobutanal, there is obtained the corresponding 1,6'-di-N-($\delta$-aminobutyl)-sisomicin.

F. 1,6'-di-N-(aminoalkyl)aminoglycosides

1. In the manner of VIII El, treat the acid addition salts of the aminoglycosides of Example VIIIB with $\beta$-acetamido-propanal or $\gamma$-acetamidobutanal to obtain the corresponding 1,6'-di-N-($\delta$-aminopropyl)aminoglycoside or 1,6'-di-N-($\gamma$-aminobutyl)aminoglycoside.

2. Alternatively, in the foregoing procedure by reacting the sulfuric acid addition salt of the 1-N-($\gamma$-acetamidopropyl) or 6'-N-($\gamma$-acetamidopropyl) derivatives of the aminoglycosides of Example VIIIB with $\beta$-acetamidopropanal, there is obtained the corresponding 1,6'-di-N-($\gamma$-aminopropyl)aminoglycoside. Similarly, by reacting the sulfuric acid addition salt of the 1-N-($\delta$-acetamidobutyl) or 6'-N-($\delta$-acetamidobutyl) derivative of the aminoglycosides of Examples VIIIB with $\delta$-acetamidobutanal there is obtained the corresponding 1,6'-di-N-($\delta$-aminobutyl)aminoglycoside.

G. In Example, VIIIA-1, by doubling the quantity of sodium cyanoborohydride, there is formed greater yields of the 1,6'-di-N-ethylsisomicin thereby formed.

EXAMPLE IX

1-N-Ethyl-6'-N-Alkylsisomicin

In the procedure of Example VIIIA-1, treat the sulfuric acid addition salt of the following aminoglycosides with acetaldehyde:

1. 6'-N-isopropylsisomicin,
2. 6'-N-t-butylsisomicin,
3. 6'-N-benzylsisomicin,
4. 6'-N-phenylethylsisomicin,
5. 6'-N-(δ-aminobutyl)sisomicin.

Isolate and purify each of the resultant products in a manner similar to that described to obtain the corresponding:

6. 1-N-ethyl-6'-N-isopropylsisomicin,
7. 1-N-ethyl-6'-N-t-butylsisomicin,
8. 1-N-ethyl-6'-N-benzylsisomicin,
9. 1-N-ethyl-6'-N-phenylethylsisomicin.
10. 1-N-ethyl-6'-N-(δ-aminobutyl)sisomicin.

PREPARATION OF 1,6'-DI-N-ALKYLAMINOGLYCOSIDES FROM THE 6'-UNSUBSTITUTED-POLY-N-ACETYL-1-N-ALKYLAMINOGLYCOSIDES

EXAMPLE X

1,6'-di-N-Ethylaminoglycosides

A. 1,6'-di-N-Ethylsisomicin

1. Dissolve 5.47 gms. of 1,3,2',3''-tetra-N-acetyl-1-N-ethylsisomicin (8.5 mmoles) in 62 ml. of 90% methanol. While stirring the solution, add 1.4 ml. of acetaldehyde (24.8 mmoles, 2.9 equivalents) and then slowly add 0.35 gms. of sodium borohydride (11 mmoles, 1.3 equivalents). Continue stirring the reaction mixture at room temperature for 3 hours, then evaporate to a residue. Dissolve the residue in a minimum of water and pass over a column (25 ml.) of IRA-401S (hydroxide form) resin. Elute with water, combine like eluates, and evaporate to a residue comprising 1,3,2',3''-tetra-N-acetyl-1,6'-di-N-ethylsisomicin.

2. Add 30 ml. of 1N sodium hydroxide to the 1,3,2',3''-tetra-N-acetyl-1,6'-di-N-ethylsisomicin residue of Example XA1 and reflux overnight. Pass the solution over a 225 ml. column of IRC-50 (proton form) resin. Elute with 3% aqueous ammonium hydroxide, evaporate the combined ammonium hydroxide eluates and chromatograph the resultant residue on silica gel eluting with the lower phase of a solvent system comprising chloroform:methanol:ammonium hydroxide (15%) (2:1:1). Monitor the fractions by thin layer chromatography on silica gel plates eluting with the lower phase of chloroform:methanol:ammonium hydroxide (28%) (1:1:1) as solvent. Pool like fractions and evaporate in vacuo to a residue comprising 1,6'-di-N-ethylsisomicin.

3. In the above procedure of Example XA1 by using as starting compound other tetra-N-alkanoyl-1-N-ethylsisomicin derivatives in place of 1,3,2',3''-tetra-N-acetyl-1-N-ethylsisomicin (e.g. 1,3,2',3''-tetra-N-propionyl-1-N-ethylsisomicin or 1,3,2',3''-tetra-N-caprylyl-1-N-ethylsisomicin), there is obtained the corresponding 1,3,2',3''-tetra-N-alkanoyl-1,6'-di-N-ethyl-sisomicin derivatives (e.g. 1,3,2'',3''-tetra-N-propionyl-1,6'-di-N-ethylsisomicin or 1,3,2',3''-tetra-N-caprylyl-1,6'-di-N-ethyl-sisomicin), each of which, upon treatment with sodium hydroxide in the manner of Example XA2 yields 1,6'-di-N-ethylsisomicin.

B. In a manner similar to that described in Example XA1 treat each of the poly-N-acetyl-1-N-ethylaminoglycosides of Preparation IVC2 (a-k) with acetaldehyde and sodium borohydride.

Isolate and purify each of the resultant products in a manner similar to that described in Example XA1 to obtain, respectively;

1. 1,3,2',3''-tetra-N-acetyl-1,6'-di-N-ethylgentamicin $C_{1a}$,
2. 1,3,3''-tri-N-acetyl-1,6'-di-N-ethylgentamicin B,
3. 1,3,2',3''-tetra-N-acetyl-1,6'-di-N-ethyl-Antibiotic JI-20A,
4. 1,3,2',3''-tetra-N-acetyl-1,6'-di-N-ethyl-Antibiotic 66-40B,
5. 1,3,2', 3''-tetra-N-acetyl-1,6'-di-N-ethyl-Antibiotic 66-40D,
6. 1,3,2', 3''-tetra-N-acetyl-1,6'-di-N-ethyltobramycin,
7. the 5-epi- and the 5-epi-azido-5-deoxy-analogs of the foregoing and of 1,3,2',3''-tetra-N-acetyl-1,6'-di-N-ethylsisomicin,
8. 1,3,2',3''-penta-N-acetyl-5-epi-amino-5-deoxy-1.6'-di-N-ethylgentamicin $C_1$ a,
9. 1,3,5,3''-tetra-N-acetyl-5-epi-amino-5-deoxy-1,6'-di-N-ethylgentamic in B,
10. 1,3,5,2',3''-penta-N-acetyl-5-epi-amino-5-deoxy-1,6'-di-N-ethyl-Antibiotic JI-20A,
11. 1,3,5,2',3''-penta-N-acetyl-5-epi-amino-5-deoxy-1,6'-di-N-ethyl-Antibiotic 66-40B,
12. 1,3,5,2',3''-penta-N-acetyl-5-epi-amino-5-deoxy-1,6'-di-N-ethyl-Antibiotic 66-40D,
13. 1,3,5,2',3''-penta-N-acetyl-5-epi-amino-5-deoxy-1,6'-di-N-ethyltobramycin,
14. 1,3,5,2',3''-penta-N-acetyl-5-epi-amino-5-deoxy-1,6'-di-N-ethylsisomicin,
15. 1,3,2',3''-tetra-N-acetyl-1,6'-di-N-ethyl-Antibiotic Mu-1,
16. 1,3,2',3''-tetra-N-acetyl-1,6'-di-N-ethyl-Antibiotic Mu-2,
17. 1,3,2',3''-tetra-N-acetyl-1,6'-di-N-ethyl-Antibiotic Mu-4, and
18. 1,3,5,2',3''-penta-N-acetyl-1,6'-di-N-ethyl-Antibiotic Mu-5.

In a manner similar to that described in Example XA2, treat each of the foregoing poly-N-acetyl-1,6'-di-N-ethylaminoglycosides with sodium hydroxide at reflux temperature. Isolate and purify each of the resultant products in a manner similar to that described in Example XA2 to obtain, respectively;

1. 1,6'-di-N-ethylgentamicin $C_1$ a,
2. 1,6'-N-ethylgentamicin B,
3. 1,6'-di-N-ethyl-Antibiotic JI-20A,
4. 1,6'-di-N-ethyl-Antibiotic 66 -40B,
5. 1,6'-di-N-ethyl-Antibiotic 66-40D,
6. 1,6'-di-N-ethyltobramycin,
7. the 5-epi and the 5-epi-azido-5-deoxy analogs of the foregoing and of 1,6'-di-N-ethylsisomicin,
8. 5-epi-amino-5-deoxy-1,6'-di-N-ethylgentamicin $C_1$ a,
9. 5-epi-amino-5-deoxy-1,6'-di-N-ethylgentamicin B,
10. 5-epi-amino-5-deoxy-1,6'-di-N-ethyl-Antibiotic JI-20A,
11. 5-epi-amino-5-deoxy-1,6'-di-N-ethyl-Antibiotic 66-40B,
12. 5-epi-amino-5-deoxy-1,6'-di-N-ethyl-Antibiotic 66-40D, 13. 5-epi-amino-5-deoxy-1,6'-di-N-ethyltobramycin,
14. 5-epi-amino-5-deoxy-1,6'-di-N-ethylsisomicin,
15. 1,6'-di-N-ethyl-Antibiotic Mu-1,
16. 1,6'-di-N-ethyl-Antibiotic Mu-2,
17. 1,6'-di-N-ethyl-Antibiotic Mu-4, and
18. 1,6'-di-N-ethyl-Antibiotic Mu-5.

EXAMPLE XI

Acid Addition Salts

A. Sulfate Salts (Sulfuric acid addition salts)

Dissolve 5.0 grams of 1,2'-di-N-ethylsisomicin or 1,6'-di-N-ethylsisomicin in 25 ml. of water and adjust the pH of the solution to 4.5 with 1N sulfuric acid. Pour into about 300 milliters of methanol with vigorous agitation, continue the agitation for about 10–20 minutes and filter. Wash the precipitate with methanol and dry at about 60° C in vacuo to obtain the corresponding 1,2'-di-N-ethylsisomicin sulfate or 1,6'-di-N-ethylsisomicin sulfate.

In like manner, the sulfate salt of the compounds of Examples VIB, C, D, VIIC, D,VIIIB, C, D, E, F may also be prepared.

B. Hydrochloride Salts

Dissolve 5.0 grams of 1,2'-di-N-ethylsisomicin or 1,6'-di-N-ethylsisomicin in 25 milliters of water. Acidify with 2N-hydrochloric acid to pH 5. Lyophilize to obtain the corresponding 1,2'-di-N-ethylsisomicin hydrochloride or 1,6'-di-N-ethylsisomicin hydrochloride.

In like manner, the hydrochloride salt of the compounds of Examples VIB, C, D, VIIC D,VIIIB, C, D, E and F may also be prepared.

The present invention includes within its scope pharmaceutical compositions comprising our novel 1,2'-di-N-X- and 1,6'-di-N-X derivatives of 4,6-di-O-(aminoglycosyl)-1,3-diaminocyclitols with a compatible, pharmaceutically acceptable carrier or coating. Also included within our invention is the method of eliciting an antibacterial response in a warm-blooded animal having a susceptible bacterial infection which comprises administering to said animal a non-toxic, antibacterially effective amount of a member selected from the group consisting of a 1,2'-di-N-X- and a 1,6'-di-N-X- derivative of a 4,6-di-O-(aminoglycosyl)-1,3-diaminocyclitol having antibacterial activity, said 4-O-aminoglycosyl having amino groups all of which are primary, said primary amino groups being on one or both of positions 2' and 6';

wherein X is a substituent selected from the group consisting of alkyl, cycloalkylalkyl, alkenyl, aralkyl, hydroxyalkyl, aminoalkyl, alkylaminoalkyl, aminohydroxyalkyl, and alkylaminohydroxyalkyl, said substituent having 2 to 8 carbon atoms and, when said substituent is substituted by both hydroxyl and amino functions, only one of said functions can be attached to any one carbon atom, and pharmaceutically acceptable acid addition salts thereof.

As discussed hereinabove, the 1,2'-di-N-X and 1,6'-di-N-X derivatives of 4,6-di-O-(aminoglycosyl)-1,3-diaminocyclitols of this invention and the non-toxic pharmaceutically acceptable acid addition salts thereof are broad spectrum antibacterial agents which, advantageously, exhibit activity against organisms, particularly gram-negative organisms, which are resistant to their 1-N-substituted precursors. Thus, the compounds of this invention can be used alone or in combination with other antibiotic agents to prevent the growth or reduce the number of bacteria in various environments. They may be used, for example, to disinfect laboratory glassware, dental and medical equipment contaminated with *Staphylococcus aureus* or other bacteria inhibited by the 1,2-di-N- and 1,6'-di-N-alkyl derivatives of this invention. The activity of the 1,2'-di-N- and 1,6'-di-N-alkyl-4,6-di-O-(aminoglycosyl)-1,3-diaminocyclitols against gram-negative bacteria renders them useful for combating infections caused by gram-negative organisms, e.g. species of Proteus and Pseudomonas. Our 1,2'-di-N- and 1,6'-di-N-alkyl-4,6-di-O-aminoglycosyl)-1,3-diaminocyclitols, e.g. 1,2'-di-N-ethylsisomicin and 1,6'-di-N-ethylsisomicin have veterinary applications, particularly in the treatment of mastitis in cattle and Salmonella induced diarrhea in domestic animals such as the dog and the cat.

In general, the dosage administered of the 1,2'-di-N- and 1,6'-di-N-alkyl-4,6-di-O-(aminoglycosyl)-1,3-diaminocyclitols will be dependent upon the age and weight of the animal species being treated, the mode of administration, and the type and severity of bacterial infection being prevented or reduced. In general, the dosage of 1,2'-di-N- and 1,6'-di-N-alkyl-4,6-di- O (aminoglycosyl)-1,3-diaminocyclitols employed to combat a given bacterial infection will be similar to the dosage requirements of the corresponding 1-N-substituted-4,6-di-O-(aminoglycosyl)-1,3-diaminocyclitols. Additionally, the 1,2'-di-N and 1,6'-di-N-alkyl4,6-di-O-(aminoglycosyl)-1,3-diaminocyclitols of our invention, particularly 1,2'-di-N-alkylsisomicins and 1,6'-di-N-alkylsisomicins wherein said alkyl has 2 to 4 carbon atoms, especially the 1,2'-di-N and 1,6'-di-N-ethyl-, 1,2'-di- and, 1,6'-di-N-propyl and 1,2'-di and 1,6'-di-N-(δ-aminobutyl)-derivatives, are also advantageously cidal against certain gram-negative organisms which are resistant to the 1-N-substituted precursors.

The 1,2'-di-N- and 1,6'-di-N-alkyl-4,6-di-O-(aminoglycosyl)1,3-diaminocyclitols and the pharmaceutically acceptable acid addition salts thereof may be administered orally. They may also be applied topically in the from of ointments, both hydrophilic and hydrophobic, in the form of lotions which may be aqueous, non-aqueous or othe emulsion type or in the form of creams. Pharmaceutical carriers useful in the preparation of such formulations will include, for example such substances as water, oils, fats, waxes, polyesters, polyols and the like.

For oral administration the 1,2'-di-N- and 1,6'-di-N-alkyl-4,6-di-O-(aminoglycosyl)-1,3-diaminocyclitols antibacterials of this invention may be compounded in the form of tablets, capsules, elixirs or the like or may even be admixed with animal feed. It is in these dosage forms that the antibacterials are most effective for treating bacterial infections of the gastrointestinal tract which infections cause diarrhea. They are also useful for pre- and post-operative gut sterilization.

In general, the topical preparations will contain from about 0.1 to about 3.0 gms. of the 1,2'-di-N- and 1,6'-di-N-alkyl-4,6-di-O (aminoglycosyl)-1,3-diaminocyclitol per 100 gms. of ointment, creams or lotion. The topical preparations are usually applied gently to lesions from about 2 to about 5 times a day.

The antibacterials of this invention may be utilized in liquid form such as solutions, suspensions the like for otic and optic use and may also be administered parenterally via intramuscular, intravenous, subcutaneous and intrasternal injection. The injectable solution or suspension will usually be administhered at from about 1 mg. to about 15 mgs. of antibacterial per kilogram of body weight per day divided into about 2 to about 4 doses. The precise dose depends on the stage and severity of the infection, the susceptibility of the infecting organism to the antibacterial and the individual characteristics of the animal species being treated.

The following formulations are to exemplify some of the dosage forms in which the antibacterial agents of this invention and their derivatives may be employed:

| | Formulation 1 | | |
|---|---|---|---|
| Tablet | 10 mg. Tab. | 25 mg. Tab. | 100 mg. Tab. |
| 1,2'-di-N or 1,6'-di-N-ethylsisomicin | 10.50 * mg. | 26.25 * mg. | 105.00 * mg. |
| Lactose, impalpable powder | 197.50 mg. | 171.25 mg. | 126.00 mg. |
| Corn Starch | 25.00 mg. | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |

* 5% excess

Procedure

Prepare a slurry consisting of the 1,2'-di-N or 1,6'-di-N-ethylsisomicin, lactose and polyvinylpyrrolidone. Spray dry the slurry. Add the corn starch and magnesium stearate. Mix and compress into tablets.

| Formulation 2 | |
|---|---|
| Ointment | |
| 1,2'-di-N- or 1,6'-di-N-ethylsisomicin | 1.0 gm. |
| Methyl paraben U.S.P. | 0.5 gm. |
| Propyl paraben U.S.P. | 0.1 gm. |
| Petrolatum to | 1000 gm. |

Procedure

1. Melt the petrolatum.
2. Mix the 1,2'-di-N or 1,6'-di-N-ethylsisomicin, methyl paraben and propyl paraben with about 10% of molten petrolatum.

We Claim:

1. A 1,2'-di-N-X and a 1,6'-di-N-X derivative of a 4,6-di-O-aminoglycosyl-1,3-diaminocyclitol having antibacterial activity, said 4-O-aminoglycosyl having amino groups, all of which are primary, said primary amino groups being on one or both of positions 2' and 6';
   wherein X is a substituent selected from the group consisting of alkyl, alkenyl, cycloalkylalkyl, aralkyl, hydroxyalkyl, aminoalkyl, alkylaminoalkyl, aminohydroxyalkyl and alkylaminohydroxyalkyl, said substituent having 2 to 8 carbon atoms, the carbon in said substituent adjacent to the aminoglycoside nitrogen being unsubstituted, and when said substituent is substituted by both amino and hydroxyl functions, only one of said functions can be attached at any one carbon atom;
   wherein the substituents, X, in said 1,2'-di-N-X- and in said 1,6'-di-N-X derivatives may be the same or different;
   and the pharmaceutically acceptable acid addition salts thereof.

2. A compound of claim 1 wherein X is a substituent having 2 to 4 carbon atoms.

3. A compound of claim 1 wherein said 6-O-aminoglycosyl is 6-O-garosaminyl and X is a substituent having 2 to 4 carbon atoms.

4. A compound of claim 1 wherein said 6-O-aminoglycosyl is 6-O-garosaminyl, said 1,3-diaminocyclitol is 2-deoxystreptamine and X is a substituent having 2 to 4 carbon atoms.

5. A compound of claim 3 which is a 1,2'-di-N-X-4-O-aminoglycosyl-6-O-garosaminyl-1,3-diaminocyclitol selected from the group consisting of:
1,2'-di-N-X-gentamicin $C_{1a}$,
1,2'-di-N-X-gentamicin $C_2$,
1,2'-di-N-X-gentamicin $C_{2a}$,
1,2'-di-N-X-gentamicin $X_2$,
1,2'-di-N-X-sisomicin,
1,2'-di-N-X-verdamicin,
1,2'-di-N-X-Antibiotic G-418,
1,2'-di-N-X-Antibiotic JI-20A,
1,2'-di-N-X-Antibiotic JI-20B,
the 5-epi, 5-epi-azido-5-deoxy, 5-epi-amino-5-deoxy analogs, of the foregoing and,
1,2'-di-N-X-Anitibiotic Mu-1,
1,2'-X-Antibiotic Mu-2,
1,2'-di-N-X-Antibiotic Mu-4,
1,2'-di-N-X-Antibiotic Mu-5,
X being a substituent having 2 to 4 carbon atoms.

6. A compound of claim 3 which is a 1,6'-di-N-X-4-O-aminoglycosyl-6-O-garosaminyl-1,3-diaminocyclitol selected from the group consisting of:
1,6'-di-N-X-gentamicin B,
1,6'-di-N-X-gentamicin $B_1$,
1,6'-di-N-X-gentamicin $C_{1a}$,
1,6'-di-N-X-gentamicin $C_2$,
1,6'-di-N-X-gentamicin $C_{2a}$,
1,6'-di-N-X-sisomicin,
1,6'-di-N-X-verdamicin,
1,6'-di-N-X-Antibiotic JI-20A,
1,6'-di-N-X-Antibiotic JI-20B,
the 5-epi, 5-epi-azido-5-deoxy, 5-epi-amino-5-deoxy analogs of the foregoing and,
1,6'-di-N-X-Antibiotic Mu-1,
1,6'-di-N-X-Antibiotic Mu-2,
1,6'-di-N-X-Antibiotic Mu-4,
1,6'-di-N-X-Antibiotic Mu-5,
X being a substituent having 2 to 4 carbon atoms.

7. A compound of claim 5 which is 1,2'-di-N-ethylsisomicin.

8. A compound of claim 5 which is 1,2'-di-N-propylsisomicin.

9. A compound of claim 5 which is 1,2'-di-N-(δ-aminopropyl)sisomicin.

10. A compound of claim 5 which is 1,2'-di-N-(δ-aminobutyl)sisomicin.

11. A compound of claim 6 which is 1,6'-di-N-ethylsisomicin.

12. A compound of claim 6 which is 1,6'-di-N-propylsisomicin.

13. A compound of claim 6 which is 1,6'-di-N-(δ-aminopropyl)sisomicin.

14. A compound of claim 6 which is 1,6'-di-N-(δ-aminobutyl)sisomicin.

15. A 2'-N-X-4,6-di-O-(aminoglycosyl)-1,3-diaminocyclitol selected from the group consisting of:
2'-N-X-gentamicin A,
2'-N-X-sisomicin,
2'-N-X-verdamicin,
2'-N-X-tobramycin,
2'-N-X-Antibiotic 66-40B, 2'-N-X-Antibiotic 66-40D,
the 5-epi, 5-epi-azido-5-deoxy, 5-epi-amino-5-deoxy analogs of the foregoing and the following;
2'-N-X-gentamicin $C_{1a}$,
2'-N-X-gentamicin $C_2$,
2'-N-X-gentamicin $C_{2a}$,
2'-N-X-gentamicin $X_2$,
2'-N-X-Antibiotic G-418,
2'-N-X-Antibiotic JI-20A,
2'-N-X-Antibiotic JI-20B,
and 2'-N-X-Antibiotic Mu-1, 2'-N-X-Antibiotic Mu-2, 2'-N-X-Antibiotic Mu-4 and 2'-N-X-Antibiotic Mu-5;
wherein X is a substituent selected from the group consisting of alkyl, alkenyl, cycloalkylalkyl, aralkyl, hydroxyalkyl, aminoalkyl, alklaminoalkyl, aminohydroxyalkyl, and alkylaminohydroxyalkyl, said substituent having 2 to 8 carbon atoms, the carbon in said substituent adjacent to the aminoglycoside nitrogen being unsubstituted and when said substituent is substituted by both hydroxyl and amino functions, only one of said functions can be attached at any one carbon atom.

16. A compound of claim 15 wherein X is a substituent having 2 to 4 carbon atoms.

17. A compound of claim 16 which is 2'-N-ethylsisomicin.

18. A compound of claim 16 which is 2'-N-propylsisomicin.

19. A compound of claim 16 which is 2'-N-butylsisomicin.

20. A compound of claim 16 which is 2'-N-(δ-aminopropyl) sisomicin.

21. A compound of claim 16 which is 2'-N-(δ-aminobutyl) sisomicin.

22. The method of eliciting an antibacterial response in a warm blooded animal having a susceptible bacterial infection which comprises administering to saidd animal a non-toxic antibacterially effective amount of a 1,2'-di-N-X and a 1,6'-di-N-X derivative of a 4,6-di-O-aminoglycosyl-1,3-diaminocyclitol having antibacterial activity, said 4-O-aminoglycosyl having amino groups all of which are primary, said primary amino groups being on one or both of positions 2' and 6';
wherein X is a substituent selected from the group consisting of alkyl, alkenyl, cycloalkylalkyl, aralkyl, hydroxyalkyl, aminoalkyl, alkylaminoalkyl, aminohydroxyalkyl and alkylaminohydroxyalkyl, said substituent having 2 to 8 carbon atoms, the carbon in aid substituent adjacent to the aminoglycoside nitrogen being unsubstituted, and when said substituent is substituted by both amino and hydroxyl functions only one of said functions can be attached at any one carbon atom;
wherein the substituents, X, in said 1,2'-di-N-X-and in said 1,6'-di-N-X derivatives may be the same or different;
and the pharmaceutically acceptable acid addition salts thereof.

23. A pharmaceutical composition comprising an antibacterially effective amount of a 1,2'-di-N-X and a 1,6'-di-N-X derivative of a 4,6-di-O-aminoglycosyl-1,3-diaminocyclitol having antibacterial activity, said 4-O-aminoglycosyl having amino groups all of which are primary, said primary amino groups being on one or both of positions 2' and 6';
wherein X is a substituent selected from the group consisting of alkyl, alkenyl, cycloalkylalkyl, aralkyl, hydroxyalkyl, aminoalkyl, alkylaminoalkyl, aminohydroxyalkyl and alkylaminohydroxyalkyl, said substituent having 2 to 8 carbon atoms, the carbon in said substituent adjacent to the aminoglycoside nitrogen being unsubstituted, and when said substituent is substituted by both amino and hydroxyl functions only one of said functions can be attached at any one carbon atom;
wherein the substituents, X, in said 1,2'-di-N-X- and in said 1,6'-di-N-X derivatives may be the same or different;
and the pharmaceutically acceptable acid addition salts thereof;
together with a non-toxic pharmaceutically acceptable carrier.

* * * * *

UNITED STATES PATENT OFFICE
CERTIFICATE OF CORRECTION

Patent No. 4,062,947  Dated December 13, 1977

Inventor(s) John J. Wright et al

It is certified that error appears in the above-identified patent and that said Letters Patent are hereby corrected as shown below:

Column 2, lines 60 and 61, " $\gamma$-ethylpentyl, $\gamma$-ethylpentyl" should read --- $\gamma$-ethylpentyl, $\delta$-ethylpentyl,---; line 62, " $\gamma$-ethylhexyl," should read --- $\delta$-ethylhexyl,---. Column 3, line 5, "such as /¯65" should read ---such as $\xi$---; line 21, " $\beta$-hydroxy-$\delta$-ethylaminopropyl," should read --- $\beta$-hydroxy-$\gamma$-ethylaminopropyl,---. Column 4, line 48, "1,2'-di-N-($\gamma$-aminobutyl)-" should read ---1,2'-di-N-($\delta$-aminobutyl)---; line 49, "-di-N-($\gamma$-aminobutyl)-" should read ---di-N-($\delta$-aminobutyl)---; line 51, "-2'-N-($\gamma$-" should read ---2'-N-($\delta$ ---; line 52, "6'-N-($\gamma$-" should read ---6'-N-($\delta$ ---; line 56, "1,2-diaminocyclitols" should read ---1,3-diaminocyclitols---. Column 6, line 6, "-O-(aminoalglycosyl)" should read ---O-(aminoglycosyl)---; lines 34 and 35, "2'-N-X, 6'-X" should read ---2'-N-X, 6'-N-X---; line 50, "2'-N-X derivatives" should read ---2'-N-X, 6'-N-X derivatives,---
Column 7, Formula I, " 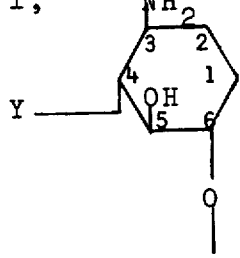 " should read --- 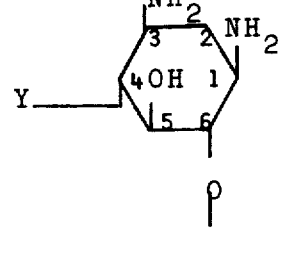 ---

Col. 19, lines 13 and 14 "IRA 401-SL (OH-)should read ---IRA 401-S (OH⁻)--- line 23, "2N aqueous hydroxide" should read ---2N aqueous ammonium hydroxide---; line 29, "E. 2'-N-($\delta$-aminopropyl)sisomicin" should read ---E. 2'-N-($\gamma$-aminopropyl)sisomicin---; line 34, "2'-N-($\delta$-amino-" should read ---2'-N-($\gamma$-amino---; line 63, "Antibiotic G-148," should read ---Antibiotic G-418,---. Column 20, line 36, "-2'-ethylsisomicin." should read ---2'-N-ethylsisomicin.---. Column 23, line 15, "-carbonyl-2-N-" should read ---carbonyl-2'-N----. Column 26, line 36, "2'-N-(S-$\delta$-amino-" should read ---2'-N-(S-$\gamma$-amino---; line 47, "-N-acetyl-1-alkylamino-" should read ---N-acetyl-1-N-alkylamino---. Column 28, line 39,

UNITED STATES PATENT OFFICE
CERTIFICATE OF CORRECTION

Patent No. 4,062,947    Dated December 13, 1977

Inventor(s) John J. Wright et al

It is certified that error appears in the above-identified patent and that said Letters Patent are hereby corrected as shown below:

"6'-N-($\delta$-acetamidopropyl)" should read ---6'-N-($\gamma$-acetamidopropyl)---; line 52, "1,6'-di-N-($\delta$-amino-" should read ---1,6'-di-N-($\gamma$-amino---; line 53, "or 1,6'-di-N-($\gamma$-amino-" should read ---or 1,6'-di-N-($\delta$-amino---. Column 29, line 66, "(e.g. 1,3,2",3"-tetra-" should read ---(e.g. 1,3,2',3"-tetra---. Column 30, line 23, "8. 1,3,2',3"-penta-" should read ---8. 1,3,5,2',3"-penta---. Column 32, line 5, "1,2-di-N- and" should read ---1,2'-di-N- and---; line 65, "suspensions the like" should read ---suspensions and the like---. Column 34, Claim 9, line 50, "-di-N-($\delta$-" should read ---di-N-($\gamma$---; line 58, Claim 13, "-di-N-($\delta$-" should read ---di-N-($\gamma$---. Column 35, Claim 20, line 32, "-2'-N-($\delta$-amino-" should read ---2'-N-($\gamma$-amino---.

Signed and Sealed this

Twenty-eighth Day of November 1978

[SEAL]

Attest:

RUTH C. MASON
Attesting Officer

DONALD W. BANNER
Commissioner of Patents and Trademarks